(12) United States Patent
Terasaka et al.

(10) Patent No.: US 6,359,145 B1
(45) Date of Patent: Mar. 19, 2002

(54) IMIDAZOLE COMPOUNDS

(75) Inventors: Tadashi Terasaka, Ikeda; Katsuya Nakamura, Takatsuki; Nobuo Seki, Takarazuka; Masako Kuno, Amagasaki; Susumu Tsujimoto, Fujiidera; Akihiro Sato, Kobe; Isao Nakanishi, Tenri; Takayoshi Kinoshita, Tsukuba; Nobuya Nishio, Yawara-mura; Hiroyuki Okumura, Osaka; Kiyoshi Tsuji, Kishiwada, all of (JP)

(73) Assignee: Fujisawa Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/764,995

(22) PCT Filed: Jul. 22, 1999

(86) PCT No.: PCT/JP99/03939

§ 371 Date: Mar. 9, 2001

§ 102(e) Date: Mar. 9, 2001

(87) PCT Pub. No.: WO00/05217

PCT Pub. Date: Feb. 3, 2000

(30) Foreign Application Priority Data

Jul. 23, 1998 (AU) ............................................. PP 4840
Nov. 27, 1998 (AU) ............................................. PP 7355

(51) Int. Cl.$^7$ ................... C07D 233/66; A61K 31/4164
(52) U.S. Cl. ............................... 548/333.5; 548/337.1; 514/400
(58) Field of Search ....................... 514/400; 548/337.1, 548/334.5

(56) References Cited

U.S. PATENT DOCUMENTS 5,096,915 A * 3/1992 Parsons et al. ............. 514/398
5,552,557 A * 9/1996 Fujii et al. ................. 548/337.1
5,703,084 A * 12/1997 Abushanab et al. ........ 514/261

FOREIGN PATENT DOCUMENTS

WO  WO 98/02166  1/1998

OTHER PUBLICATIONS

G. Cristalli, et al., Journal of Medicinal Chemistry, vol. 34, No. 3, pp. 1187–1192, "Adenosine Deaminase inhibitors: Synthesis and Structure–Activity Relationships of Imidazole Analogues of Erytro–9–(2–Hydroxy–3–Nonyl)Adenine", Mar. 1991.

G. Cristalli, et al., Drug Development Research, vol. 28, No. 3, pp. 253–258, "Adenosine Deaminase Inhibitors: Structure–Activity Relationships in 1–Deazaadenosine and Erythro–9–(2–Hydroxy–3–Nonyl)Adenine Analogues", 1993.

C. Vargeese, et al., Journal of Medicinal Chemistry, vol. 37, No. 22, pp. 384–3849, "Adenosine Deaminase Inhibitors. Synthesis and Biological Evaluation of Putative Metabolites of (+)–Erythro–9–(2S–Hydroxy–3R–Nonyl)Adenine", Oct. 28, 1994.

L. B. Piotrovskii, et al., Russian Journal of General Chemistry, vol. 67, No. 5, pp. 801–804, "Alkylation of Imidazole–4(5)–Carboxylic Acid Derivatives with Ethylene Oxide", May, 1997.

Chemical Abstracts, vol. 93, No. 15, an 142660J, p. 22 and 1977–1981 Chem. Substance Index page, "Ethyl 4 (5)–Imidazolecarboxylate (Code No. C–751) as an Orally Effective Chemotherapeutic Agent Against Leptospirosis", 1980.

* cited by examiner

*Primary Examiner*—Floyd D. Higel
*Assistant Examiner*—Golam M. M. Shameem
(74) *Attorney, Agent, or Firm*—Oblon, Spivak, McClelland, Maier & Neustadt, P.C.

(57) ABSTRACT

Imidazole compounds having adenosine deaminase inhibitory activity represented by formula (I) wherein $R^1$ is hydrogen, hydroxy, protected hydroxy, or aryl optionally substituted with suitable substituent(s); $R^2$ is hydrogen or lower alkyl; $R^3$ is hydroxy or protected hydroxy; $R^4$ is cyano, (hydroxy)iminoamino(lower)alkyl, carboxy, protected carboxy, heterocyclic group optionally substituted with amino, or carbamoyl optionally substituted with suitable substituent(s); and —A— is —Q— or —O—Q—, wherein Q is single bond or lower alkylene, provided that when $R^2$ is lower alkyl, then $R^1$ is hydroxy, protected hydroxy, or aryl optionally substituted with suitable substituent(s), its prodrug, or their salt. The compounds are useful for treating and/or preventing diseases for which adenosine is effective.

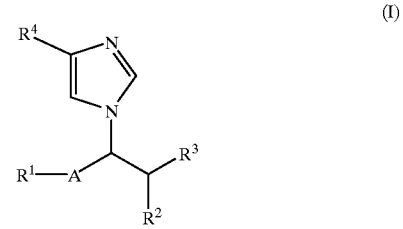

(I)

11 Claims, No Drawings

IMIDAZOLE COMPOUNDS

This application is a 371 of PCT/JP99/03939 Jul. 22, 1999.

TECHNICAL FIELD

This invention relates to novel imidazole compounds having pharmacological activity, to a process for their production and to a pharmaceutical composition containing the same.

BACKGROUND ART

Adenosine (Ado) is an endogenous purine nucleoside released by cells as part of the normal metabolic machinery. Ado has wide variety of biological activities, namely potent antiinflammatory and immunosuppressive properties, protective effects in cardiovascular and cerebrovascular ischemia, anticonvulsant effects and modulation effects of platelet aggregation, lipolysis, glycogenesis, blood flow and neurotransmission. Ado shows the biological activities by binding to its receptors anchored in the cell membrane. Therefore, it is the beneficial treatment for many diseases to perform the pharmacological elevation of extracellular Ado concentrations.

Adenosine deaminase (ADA) catalyzes an essentially irreversible deamination of adenosine or deoxyadenosine to inosine or deoxyinosine, respectively. In the last 10 years, ADA, which was considered to be cytosolic, has been found on the cell surface of many cells. Thus, blocking ADA activity with specific inhibitor is the potent way to elevate Ado concentrations in biological systems and the beneficial treatment for many diseases.

Some compounds have known to have inhibitory activity of ADA (J. Med. Chem. 27, 274–278, 1984; ibid. 31, 390–393, 1988; ibid. 34, 1187–1192, 1991; ibid. 35, 4180–4184, 1992; ibid. 37, 305–308, 1994; ibid. 37, 3844–3849, 1994; and WO98/02166).

Known imidazole compounds with pharmaceutical activity other than ADA inhibitory activity are described in U.S. Pat. No. 4,451,478 and WO97/26883.

Furthermore, some imidazole derivatives having ADA inhibitory activity have been reported, for example, as described in Drug Developement Research 28, 253–258, 1993.

DISCLOSURE OF THE INVENTION

This invention relates to novel imidazole compounds, which have pharmaceutical activity such as ADA inhibiting activity, to a process for their production, to a pharmaceutical composition containing the same and to a use thereof.

One object of this invention is to provide the novel imidazole compounds, which have an ADA inhibiting activity.

Another object of this invention is to provide a process for production of the imidazole compounds.

A further object of this invention is to provide a pharmaceutical composition containing the imidazole compound as an active ingredient.

Still further object of this invention is to provide a use of the imidazole compound for manufacturing a medicament for treating or preventing various diseases, or a method of treating or preventing various diseases by administering the imidazole compound in an effective amount to elevate adenosine concentration.

The imidazole compounds of this invention can be represented by the following formula (I):

(I)

[Structure of compound (I): imidazole ring with $R^4$ substituent, connected via N to a carbon bearing $R^3$ and another carbon bearing $R^2$ and $R^1$—A—]

wherein $R^1$ is hydrogen, hydroxy, protected hydroxy, or aryl optionally substituted with suitable substituent(s);

$R^2$ is hydrogen or lower alkyl;

$R^3$ is hydroxy or protected hydroxy;

$R^4$ is cyano, (hydroxy)iminoamino(lower)alkyl, carboxy, protected carboxy, heterocyclic group optionally substituted with amino, or carbamoyl optionally substituted with suitable substituent(s); and —A— is —Q— or —O—Q—, wherein Q is single bond or lower alkylene, provided that when $R^2$ is lower alkyl, then $R^1$ is hydroxy, protected hydroxy, or aryl optionally substituted with suitable substituent(s), its prodrug, or their salt.

The compound (I), its prodrug, or their salt can be prepared by the following processes. In the following formulae, compounds may be prodrugs or their salts.

Process 1

(III) + (IV) → (I)

wherein $R^1$, $R^2$, $R^3$, $R^4$, and A re each as defined above, and X is hydroxy or a leaving group, provided that $R^3$ is not hydroxy.

In this process the compound (I) can be produced by reacting the compound (IV), where X is hydroxy, with alkanesulfonyl chloride (i.e., methanesulfonyl chloride, etc.) or arylsulfonyl chloride (i.e., toluenesulfonyl chloride, etc.) in the presence of a base such as triethylamine or pyridine in a solvent such as dichloromethane, chloroform, tetrahydrofuran, or diethyl ether from 0° C. to room temperature for about 1 hour and reacting the resulting sulfonate with the compound (III) in the presence of a base such as sodium hydride, potassium tert-butoxide, or potassium carbonate in a solvent such as dimethylformamide (DMF) from room temperature to 100° C. for 5 to 100 hours. Alternatively, the compound (III) can be reacted with the compound (IV) in the presence of a base such as sodium methoxide, potassium tert-butoxide, or sodium hydride to give the compound (I).

The compound (I) wherein $R^3$ is hydroxy can be obtained by the following process:

Process 2

(II) → (I-1)
Reduction

In the reaction formula $R^1$ and $R^4$ are as defined above and R' is a hydroxy protective group.

In process 2, the compound (I-1) can be produced by reducing the compound (II) using a reducing agent such as sodium borohydride in a solvent such as methanol, ethanol, tetrahydrofuran, or water at 0° C. to reflux temperature for 30 minutes to 72 hours.

When the compound (I) contains a protected hydroxy group, the protected hydroxy group can be converted to a hydroxy group by a known method, for example, by reacting the compound with a deprotecting agent such as palladium hydroxide on carbon/cyclohexane, iodotrimethylsilane or tetrabutylammonium fluoride in a solvent such as ethanol, chloroform or tetrahydrofuran.

The compound (I) where $R^4$ is (hydroxy)iminoamino(lower)alkyl, heterocyclic group or substituted carbamoyl can be prepared from the compound (I) where $R^4$ is cyano or protected carboxy by reacting the latter with the compound corresponding to $R^4$ of the former with or without a condensing agent such as sodium methoxide at room temperature to 120° C. for 2 to 72 hours.

The starting compound (II) can be prepared by the following reaction.

(III) + (IV-1) → (II)

In the reaction formula $R^1$, $R^4$, R', and A are as defined above.

This reaction can be performed in the same manner as in Process 1.

In the following, suitable examples of the definitions to be included within the scope of the invention are explained in detail.

The term "lower" means a group having 1 to 6 carbon atom(s), unless otherwise provided.

Suitable "lower alkyl" and lower alkyl moiety of "lower alkoxy" include a straight or branched one such as methyl, ethyl, propyl, isopropyl, butyl, isobutyl, tert-butyl, pentyl, hexyl, or the like, with methyl being preferred.

Suitable "lower alkylene" may be straight or branched one having 1 to 8. carbon atom(s), such as methylene, ethylene, trimethylene, tetramethylene, pentamethylene, hexamethylene, or the like.

Suitable "protected hydroxy" includes lower alkoxy optionally substituted with aryl; acyloxy; or tri(lower) alkylsilyloxy (i.e., trimethylsilyloxy, tert-butyldimethylsilyloxy, etc.); or the like.

Suitable hydroxy protective groups in the protected hydroxy group include lower alkyl optionally substituted with aryl; acyloxy; tri(lower)alkylsilyloxy (i.e., trimethylsilyloxy, tert-butyldimethylsilyloxy, etc.); or the like.

Suitable "halogen" includes fluorine, chlorine, bromine, or iodine.

Suitable "aryl" and aryl moeity of "aroyl" include phenyl, naphthyl, tolyl, xylyl, or the like, with phenyl and naphthyl being preferred.

Suitable "protected carboxy" includes lower alkoxycarbonyl (e.g., methoxycarbonyl, ethoxycarbonyl, propoxycarbonyl, butoxycarbonyl, 2,2,2-trichloroethoxycarbonyl, etc.), aryloxy-carbonyl (e.g., phenoxycarbonyl, 4-nitrophenoxycarbonyl, etc.), ar(lower) alkoxycarbonyl (e.g. benzyloxycarbonyl, 4-nitrobenzyloxycarbonyl, etc.), or the like.

Suitable carboxy protective groups in the protected carboxy group include lower alkyl (e.g., methyl, ethyl, or tert-butyl), halo(lower)alkyl (e.g., 2-iodomethyl or 2,2,2-trichloroethyl), ar(lower)alkyl (e.g., benzyl, trityl, 4-methoxybenzyl, 4-nitrobenzyl, phenethyl, bis(methoxyphenyl)methyl, 3,4-dimethoxybenzyl or 4-hydroxy-3,5-di-tert-butylbenzyl), aryl (e.g., phenyl, naphthyl, tolyl, or xylyl), and the like. More suitable examples are lower alkyl such as methyl, ethyl, or tert-butyl, and ar(lower)alkyl such as benzyl.

Suitable "acyl" and acyl moiety of "acyloxy" include lower alkanoyl, aroyl, or the like.

Suitable "lower alkanoyl" includes formyl, acetyl, propionyl, butyryl, isobutyryl, valeryl, isovaleryl, pivaloyl, hexanoyl, or the like.

Suitable "aroyl" may be benzoyl, naphthoyl, toluoyl, xyloyl, or the like.

In the definition, unless stated otherwise, "lower alkanoyl" and "aroyl" may be substituted with one or more substituent(s) selected from halogen, cyano, nitro, lower alkyl, and a combination thereof.

Suitable "acyloxy" includes acetyloxy, trifluoroacetyloxy, or the like.

Suitable "leaving group" may be halogen, acyloxy (e.g., acetyloxy, trifluoroacetyloxy, etc.), lower alkylsulfonyloxy (e.g., methanesulfonyloxy, etc.), triarylphosphinoxy (e.g., —O—P$^+$(C$_6$H$_5$)$_3$, etc.), or the like.

Suitable "substituent(s)" of "carbamoyl" include amino, hydroxy, lower alkyl, lower alkylsulfonyl, and aminoimino(lower)alkyl optionally substituted with hydroxy, or the like.

Suitable "substituent(s)" of "aryl" include lower alkyl optionally substituted with hydroxy or protected carboxy; lower alkoxy optionally substituted with aryl; hydroxy; amino; acyl; halogen; carboxy; protected carboxy; carbamoyl; lower alkylenedioxy, or the like.

Suitable "heterocyclic group" contains at least one hetero atom selected from nitrogen, sulfur, and oxygen atom and may be saturated or unsaturated, monocyclic or polycyclic heterocyclic group. Preferable examples of the heterocyclic group include N-containing heterocycyclic group described below.

(1) unsaturated 3 to 7-membered, preferably 5- or 6-membered heteromonocyclic group containing I to 4 nitrogen atoms, for example, pyrrolyl, pyrrolinyl, imidazolyl, pyrazolyl, pyridyl, pyrimidinyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

(2) saturated 3 to 7-membered, preferably 5- or 6-membered heteromonocyclic group containing 1 to 4 nitrogen atoms (e.g., pyrrolidinyl, imidazolidinyl, piperidyl, piperazinyl, etc.);

(3) unsaturated 3 to 7-membered, preferably 5- or 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,2,4-oxadiazolinyl, 1,3,4-oxadiazolyl, 1,2,5-oxadiazolyl, etc.), etc.;

(4) saturated 3 to 7-membered, preferably 5- or 6-membered heteromonocyclic group containing 1 to 2 oxygen atoms and 1 to 3 nitrogen atoms (e.g., morpholinyl, etc.);

(5) unsaturated 3 to 7-membered, preferably 5- or 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.), etc.;

(6) saturated 3 to 7-membered preferably 5- or 6-membered heteromonocyclic group containing 1 to 2 sulfur atoms and 1 to 3 nitrogen atoms (e.g., thiomorpholinyl, thiazolidinyl, etc.) and the like.

Among the above, more preferable heterocyclic group included in $R^4$ is above-mentioned (1), in which the most preferable one is triazolyl or tetrazolyl.

Suitable salts of the compounds of the present invention are pharmaceutically acceptable conventional non-toxic salts and can be an organic acid addition salt (e.g. formate, acetate, trifluoroacetate, maleate, tartarate, oxalate, methanesulfonate, benzenesulfonate, toluenesulfonate, etc.), an inorganic acid addition salt (e.g. hydrochloride, hydrobromide, sulfate, phosphate, etc.), a salt with an amino acid (e.g. aspartic acid salt, glutamic acid salt, etc.), or the like.

The "prodrug" means the derivatives of compounds of the present invention having a chemically or metabolically degradable group, which becomes pharmaceutically active after biotransformation.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

Also included in the scope of invention are radiolabelled derivatives of compounds of formula (I) which are suitable for biological studies.

The compound of the present invention can be purified by any conventional purification methods employed for purifying organic compounds, such as recrystallization, column chromatography, thin-layer chromatography, high-performance liquid chromatography and the like. The compounds can be identified by conventional methods such as NMR spectrography, mass spectrography, IR spectrography, elemental analysis, and measurement of melting point.

The compound (I), its prodrug, or their salt can be administered alone or in the form of a mixture, preferably, with a pharmaceutical vehicle or carrier.

The active ingredient of this invention can be used in the form of a pharmaceutical preparation, for example, in solid, semisolid or liquid form, which contains a compound (I), as an active ingredient, in admixture with an organic or inorganic carrier or excipient suitable for external (topical), enteral, intravenous, intramuscular, parenteral or intramucous applications. The active ingredient can be formulated, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paster, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient can be formulated into, for example, preparations for oral application, preparations for injection, preparations for external application, preparations for inhalation, preparations for application to mucous membranes.

Mammals which may be treated by the present invention include livestock mammals such as cows, horses, etc., domestic animals such as dogs, cats, rats, etc. and humans, preferably humans.

While the dosage of therapeutically effective amount of the compound (I) will vary depending upon the age and condition of each individual patient, an average single dose to a human patient of about 0.01 mg, 0.1 mg, 1 mg, 10 mg, 50 mg, 100 mg, 250 mg, 500 mg, and 1000 mg of the compound (I) may be effective for treating the above-mentioned diseases. In general, amounts between 0.01 mg/body and about 1,000 mg/body may be administered per day.

The compound (I) or its pharmaceutically acceptable salts of this invention possesses ADA inhibiting activity and are thus useful in immunomodulation, especially immunosuppression, antiinflammation and treatment and prevention of various diseases for which Ado is effective. Examples of the diseases are as follows:

a) Autoimmune diseases and inflammatory conditions, e.g., various pains collagen diseases, autoimmune diseases, various immunity diseases, and the like in human beings or animals, and more particularly for the treating and/or preventing inflammation and pain in joint and muscle (e.g. rheumatoid arthritis, rheumatoid spondylitis, osteoarthritis, gouty arthritis, etc.), inflammatory skin condition (e.g. sunburn, eczema, etc.), inflammatory eye condition (e.g. conjunctivitis, etc.), lung disorder in which inflammation is involved (e.g. asthma, bronchitis, pigeon fancier's disease, farmer's lung, etc.), condition of the gastrointestinal tract associated with inflammation (e.g. aphthous ulcer, Crohn's disease, atrophic gastritis, ulcerative colitis, coeliac disease, regional ileitis, irritable bowel syndrome, etc.), gingivitis, (inflammation, pain and tumescence after operation or injury), pyrexia, pain and other conditions associated with inflammation, systemic lupus erythematosus, scleroderma, polymyositis, polychondritis, periarteritis nodosa, ankylosing spondylitis, inflammatory chronic renal condition (e.g.

nephrotic syndrome, glomerulonephritis, membranous nephritis, etc.), acute nephritis, rheumatic fever, Sjogren's syndrome, Behcet disease, thyroiditis, type I diabetes, dermatomyositis, chronic active hepatitis, acute hepatitis, myasthenia gravis, idiopathic sprue, Grave's disease, multiple sclerosis, primary billiary cirrhoris, Reiter's syndrome, autoimmune hematological disorders (e.g. hemolytic anemia, pure red cell anemia, idiopathic thrombocytopenia; aplastic anemia, etc.), myasthenia gravis, uveitis, contact dermatitis, psoriasis, Kawasaki disease, sarcoidosis, Wegner's granulomatosis, Hodgkin's disease, or the like;

b) Organ or tissue allo-or xeno-transplant rejection, e.g., kidney, liver, heart, lung, combined heart-lung, bone marrow, islet cells, pancreatic, skin, chromaffin or dopamine producing cells, small bowel, or corneal transplantation. Treating and/or preventing graft-versus-host disease, such as occurs following bone marrow transplantation;

c) Various leukemias, including virus induced, or various induced lymphomas; and d) Diseases that arise from, or are aggravated by, insufficient blood flow through a particular organ or portion thereof, e.g., heart attacks or strokes, the microvascular disease of diabetes mellitus, atherosclerosis, or events resulting in a less prolonged loss of blood flow (e.g., angina pectoris, transient ischemic attacks, bowel ischemia, kidney ischemia, intermittant claudication of skeletal muscle, migraine headaches, Raynaud's phenomenon), or the like.

Any patents, patent applications, and publications cited herein are incorporated by reference.

In order to illustrate the usefulness of the object compound (I), the pharmacological test data of the compound (I) are shown in the following.

Adenosine Deaminase (ADA) Enzyme Assay
Test Compound 1-(1-Hydroxy-4-phenyl-2-butyl)imidazole-4-carboxamide (Example 1)

Test Method

The reaction velocity (V) is measured by a change in absorbance at 265 nm (A265) resulting from the deamination of adenosine. Human ADA was expressed and purified from ADA-deficient bacterial strain. Reaction mixtures in a total volume of 200 µl contained 25 mU/ml of ADA and varying concentrations of adenosine and test compounds in 10 mM phosphate buffer saline (pH 7.4). The reaction was started by addition of ADA to a mixture of adenosine and test compound. The reaction was followed at room temperature by recording decrease in A265 for 5 minutes in SPECTRAmax 250 (Molecular Devices, USA) to automatically calculate Vmax. The inhibition constant (Ki) values of test compounds were determined by Dixon plot.

Results
Test Compound: Ki=5.9 µM

Endotoxin-induced Cytokine Production
Test Compound 1-(1-Hydroxy-4-phenyl-2-butyl)imidazole-4-carboxamide Test Method BALB/c mice (male, 7 weeks old) were injected i.v. with 0.1 mg/kg of lipopolysaccharides (LPS) in a total volume of 0.2 ml saline. Heparinized blood samples were taken one hour after LPS injection and plasma was collected by centrifugation. TNF-α (inflammatory cytokine) and IL-10 (anti-inflammatory cytokine) amounts in plasma were assayed by ELISA. Test compounds were administered 30 minutes before LPS injection.

Results

|  | TNF-α (ng/ml) | IL-10 (pg/ml) |
|---|---|---|
| Vehicle | 4.7 ± 0.4 | 71 ± 9.2 |
| Test Compound (320 mg/kg) | 3.1 ± 0.5 | 137 ± 14 |

BEST MODE FOR CARRYING OUT THE INVENTION

The following Preparation and Examples are given for the purpose of illustrating the present invention in detail, but are not to be construed to limit the scope of the present invention.

Preparation 1

A mixture of methyl 4-imidazolecarboxylate (5.0 g) and ammonium chloride (539 mg) in aqueous 28% $NH_3$ solution (75 ml) was heated at 100° C. in a steel sealed tube for 5.5 hours. After cooling, the reaction mixture was concentrated in vacuo. The residue was stirred in a mixed solvent of acetone, ethanol and water (5:5:1, total 25 ml). The resulting precipitates were collected by filtration and washed with the same mixed solvent, and dried in vacuo to give 4-imidazolecarboxamide (4.63 g) as a white solid.

mp: 211–214° C.

IR (KBr): 3500–2600, 1652 $cm^{-1}$

NMR (DMSO-$d_6$, δ): 7.06 (1H, br s), 7.34 (1H, br s), 7.58 (1H, s), 7.69 (1H, s)

MASS: 112 $(M+H)^+$

Preparation 2

Triethylamine (583 mg) was added dropwise to a stirred mixture of ethyl (R)-2-hydroxy-4-phenylbutyrate (1.0 g) and methanesulfonyl chloride (660 mg) in dichloromethane (10 ml) at ice-bath temperature. After 40 minutes, the reaction mixture was partitioned between dichloromethane and water. The organic layer was washed with brine, dried over magnesium sulfate, and concentrated in vacuo to give ethyl (R)-2-methylsulfonyloxy-4-phenylbutyrate (1.37 g) as an oil. This material was used immediately without further purification. NaH (60% in mineral oil, 192 mg) was added to a solution of 4-imidazolecarboxamide (534 mg) in DMF (8 ml) at room temperature. The reaction mixture was stirred for 30 minutes. The methanesulfonate prepared above was added and the resulting mixture was stirred for 3 hours at 60° C.

The reaction mixture was cooled to 10° C. in an ice bath, and the insoluble material was filtered and washed thoroughly with methylene chloride. The filtrate and the washing were combined and then washed with brine. The organic layer was dried over sodium sulfate and concentrated in vacuo. The residue was purified by silica gel (45 g) chromatography eluting with chloroform/methanol (30:1) to give ethyl 2-(4-carbamoyl-1-imidazolyl)-4-phenylbutyrate (556 mg).

IR (neat): 3500–2800, 1741, 1666 $cm^{-1}$

NMR ($CDCl_3$, δ): 1.26 (3H, t, J=7.1 Hz), 2.3–2.68 (4H, m), 4.20 (3H, q, J=7.1 Hz), 4.60 (1H, dd, J=9.8, 9.8 Hz), 5.44 (1H, br s), 6.96 (1H, br s), 7.08–7.35 (5H, m), 7.46 (1H, s), 7.72 (1H, s) MASS: 302 $(M+H)^+$

Preparation 3

2-Hydroxyoctanoic acid (1.0 g) was stirred in 10% hydrogen chloride methanol solution (20 ml) at room temperature.

After 1.5 hours, the reaction mixture was evaporated under reduced pressure. The residue was partitioned between ethyl acetate and water. The organic layer was washed with aqueous NaHCO$_3$ solution and dried over sodium sulfate. Evaporation of the solvent under reduced pressure gave methyl 2-hydroxyoctanoate (0.684 g) as a colorless oil.

IR (neat): 3463, 2952, 2927, 2859, 1735 cm$^{-1}$

NMR (CDCl$_3$,δ): 0.88 (3H, t, J=6.5 Hz), 1.25–1.90 (10H, m), 2.70 (1H, br s), 3.79 (3H, s), 4.19 (1H, br)

MASS: 175 (M+H)$^+$

Preparation 4

The following compounds were obtained according to a similar manner to that of Preparation 2.

(1) Methyl α-(4-carbamoyl-1-imidazolyl)phenylacetate was prepared from methyl mandelate and 4-imidazolecarboxamide obtained in Preparation 1.

IR (KBr): 3500–2800, 1752, 1675 cm$^{-1}$

NMR (CDCl$_3$,δ): 3.84 (3H, s), 5.48 (1H, br s), 5.93 (1H, s), 7.06 (1H, br s), 7.24–7.46 (5H, m), 7.60 (1H, s), 7.67 (1H, s)

MASS: 260 (M+H)$^+$ (2) Methyl 2-(4-carbamoyl-1-imidazolyl)octanoate was prepared from 4-imidazolecarboxamide obtained in Preparation 1 and methyl 2-hydroxyoctanate obtained in Preparation 3.

mp: 63.5–65.5° C.

IR (KBr): 3400–2800, 1753, 1671 cm$^{-1}$

NMR (CDCl$_3$,δ): 0.87 (3H, t, J=6.5 Hz), 1.05–1.45 (6H, m), 1.90–2.20 (4H, m), 3.77 (3H, s), 4.71 (1H, dd, J=9.6, 5.6 Hz), 5.52 (1H, s), 7.10 (1H, s), 7.59 (1H, s), 7.72 (1H, s)

MASS: 268 (M+H)$^+$

Preparation 5

NaH (60% in mineral oil, 60 mg) was added to a stirred solution of 4-imidazolecarboxamide (obtained in Preparation 1) (167 mg) in DMF (3.5 ml), and the reaction mixture was stirred for 1.5 hours at 55° C. Ethyl 2-bromovalerate (0.153 ml) was added to this mixture, and the reaction mixture was stirred for 3 hours at 55–60° C. The reaction mixture was poured into water and extracted with ethyl acetate. The organic layer was washed with brine, dried over magnesium sulfate, and concentrated in vacuo. The residue was purified by silica gel (12 g) chromatography eluting with chloroform/methanol (25:1) to give ethyl 2-(4-carbamoyl-1-imidazolyl)valerate (150 mg).

mp: 95° C.

IR (KBr): 3343, 3197, 2964, 1751, 1681 cm$^{-1}$

NMR (DMSO-d$_6$,δ): 0.86 (3H, t, J=7.2 Hz), 1.13 (2H, m), 1.20 (3H, t, J=7.1 Hz), 2.05 (2H, q, J=7.2 Hz), 4.14 (2H, q, J=7.1 Hz), 5.16 (1H, t, J=7.2 Hz), 7.10 (1H, s), 7.30 (1H, s), 7.73 (1H, s), 7.78 (1 H, s)

MASS: 240 (M+H)$^+$

Preparation 6

1-(2-Oxotetrahydrofuran-3-yl)imidazole-4-carboxamide was obtained from 4-imidazolecarboxamide obtained in Preparation 1 and α-bromo-γ-butyrolactone according to a similar manner to that of Preparation 5.

IR (KBr): 3700–3100, 1779, 1745, 1600 cm$^{-1}$

MASS: 196 (M+H)$^+$

Preparation 7

Trifluoromethanesulfonic acid (1.13 g) was added to a stirred mixture of ethyl (S)-(−)-lactate (5.90 g) and benzyl 2,2,2-trichloroacetimidate (15.15 g) in cyclohexane (70 ml) and methylene chloride (35 ml) at room temperature under nitrogen atmosphere. After being stirred for 18 hours, the reaction mixture was filtered. The filtrate was diluted with cyclohexane, and then washed successively with saturated NaHCO$_3$ solution (100 ml) and H$_2$O (100 ml). The organic layer was dried over sodium sulfate and concentrated in vacuo. The residue was purified by silica gel (260 g) chromatography eluted with hexane/ethyl acetate (30:1) to give ethyl (S)-2-(benzyloxy)propionate (6.48 g).

IR (neat): 3100–2800, 1743, 1139 cm$^{-1}$

NMR (CDCl$_3$,δ): 1.26 (3H, t, J=7.0 Hz), 1.44 (3H, d, J=6.8 Hz), 4.05 (1H, q, J=6.8 Hz), 4.22 (2H, q, J=7.0 Hz), 4.40–4.75 (2H, m), 7.10–7.39 (5H, m)

MASS: 231 (M+Na)$^+$

[α]$^{28.5}$=−76.0° (C=0.50, EtOH)

Preparation 8

A solution of 1.0M DIBAL (diisobutylaluminum hydride) in hexane (10 ml) was added dropwise to a stirred solution of ethyl (S)-2-(benzyloxy)propionate (obtained in Preparation 7) (2.08 g) in methylene chloride (20 ml) at −78° C. (dry-ice/acetone) for 5 minutes under nitrogen atmosphere. After 20 minutes, methanol (1.6 ml) was added dropwise to the mixture at −78° C., and the resulting mixture was stirred at room temperature for 30 minutes. The mixture was filtered through a pad of Celite, and the solid on the filter was washed with methylene chloride. The combined filtrates were concentrated in vacuo. The obtained residue was purified by silica gel (35 g) chromatography eluted with hexane/ethyl acetate (30:1) to give (S)-2-(benzyloxy) propionaldehyde (810 mg).

IR (neat): 3100–2800, 1735, 1095 cm$^{-1}$

NMR (CDCl$_3$,δ): 1.33 (3H, d, J=6.9 Hz), 3.90 (1H, m), 4.60 (2H, m), 7.10–7.40 (5H, m), 9.67 (1H, s)

MASS: 163 (M−H)$^+$

[α]$^{26.8}$=−34.7° (C=0.50, EtOH)

Preparation 9

Trimethylsulfoxonium iodide (1.22 g) was added to a stirred suspension of sodium hydride (60% in mineral oil, 234 mg) in dimethylsulfoxide (12 ml) and dimethoxyethane (10 ml) at −3° C. to −4° C. under nitrogen atmosphere. After 10 minutes, a solution of (S)-2-(benzyloxy)propionaldehyde (obtained in Preparation 8) (800 mg) in dimethoxyethane (2 ml) was added dropwise to the mixture for a period of 5 minutes at the same temperature, and the resulting mixture was stirred for 30 minutes at room temperature. The mixture was poured into a cold saturated ammonium chloride solution (50 ml) and extracted with ethyl acetate (100 ml). The organic layer was washed with brine (50 ml), dried over magnesium sulfate and concentrated in vacuo. The residue was purified by silica gel (20 g) chromatography eluted with hexane/ethyl acetate (30:1) to give (3S)-3-benzyloxy-1,2-epoxybutane (507 mg).

IR (neat): 2981, 2927, 2865, 1241, 1103 cm$^{-1}$

NMR (CDCl$_3$,δ): 1.29 (3H, m), 2.40–3.55 (4H, m), 4.50–4.85 (2H, m), 7.10–7.40 (5H, m)

MASS: 201 (M+Na)$^+$

Preparation 10

A solution of 2.0M benzylmagnesium chloride in tetrahydrofuran (2.38 ml) was added dropwise to a stirred mixture of lithium chloride (20.2 mg) and copper(II) chloride (32 mg) in tetrahydrofuran (10 ml) at −78° C. (dry-ice/acetone) for a period of 10 minutes under nitrogen atmosphere. A solution of (3S)-3-benzyloxy-1,2-epoxybutane (obtained in Preparation 9) (425 mg) in tetrahydrofuran (10 ml) was added dropwise to this mixture at −78° C. over 10 minutes. The resulting mixture was stirred at −78° C. for 2.5 hours and then allowed to warm to room temperature, and stirred overnight. The reaction mixture was treated with saturated ammonium chloride solution (20 ml) at an ice-bath temperature, and then diluted with ethyl acetate (100 ml). The organic layer was washed with H$_2$O (50 ml) and brine (50 ml), dried over magnesium sulfate and concentrated in vacuo. The residue was purified by silica gel (20 g) chromatography eluted with hexane/ethyl acetate (10:1) to give (2S)-2-benzyloxy-5-phenylpentan-3-ol (620 mg).

IR (neat): 3444, 2931, 2865 cm$^{-1}$

NMR (CDCl$_3$,δ): 1.14–2.00 (3H, m), 1.60–1.85 (1H, m), 2.55–3.00 (3H, m), 3.30–3.85 (3H, m), 4.35–4.75 (2H, m), 7.05–7.40 (10H, m)

MASS: 293 (M+Na)$^+$

Preparation 11

The following compounds were obtained according to a similar manner to that of Preparation 10.

(1) (2S)-2-benzyloxy-6-phenylhexan-3-ol was prepared from (3S)-3-benzyloxy-1,2-epoxybutane (obtained in Preparation 9) and phenethylmagnesium chloride.

IR (neat): 3436, 2933, 2861 cm$^{-1}$

NMR (CDCl$_3$,δ): 1.05–1.20 (3H, m), 1.30–2.00 (4H, m), 2.00–2.80 (3H, m), 3.25–3.85 (2H, m), 4.35–4.75 (2H, m), 7.05–7.45 (10H, m)

MASS: 285 (M+Na)$^+$ (2) (2S)-2-benzyloxy-5-(1-naphthyl)pentan-3-ol was prepared from (3S)-3-benzyloxy-1,2-epoxybutane (obtained in Preparation 9) and 1-naphthylmethylmagnesium chloride (J. Am. Chem. Soc. 1943, 65, 295).

IR (neat): 3700–3100, 3100–2800, 1087, 1076 cm$^{-1}$

NMR (CDCl$_3$,δ): 1.10–1.20 (3H, m), 1.75–2.00 (2H, m), 2.15–2.75 (1H, m), 2.95–3.95 (4H, m), 4.40–4.75 (2H, m), 7.20–7.60 (9H, m), 7.65–7.20 (3H, m)

(3) (2S,3S)-2-(benzyloxy)-5-(2-methylphenyl)pentan-3-ol was prepared from the compound obtained in Preparation 9 and 2-methylbenzyl chloride.

NMR (CDCl$_3$, δ): 1.19 (3H, d,J=6 Hz), 1.6–1.8 (2H, m), 2.32 (3H, s), 2.64 (1H,d,J=3 Hz), 2.6–3.0 (2H,m), 3.3–3.6 (2H,m), 4.43 (1H,d,J=l11 Hz), 4.67 (1H,d,J=11 Hz), 7.1–7.3 (9H, m)

MASS: 307 (M+Na)$^+$ (4) (2S,3S)-2-(benzyloxy)-5-(2-chlorophenyl)pentan-3-ol was prepared from the compound obtained in Preparation 9.

NMR (CDCl$_3$, δ): 1.17 (3H, d,J=5 Hz), 1.6–1.9 (2H, m), 2.64 (1H,d,J=3 Hz), 2.7–3.1 (2H,m), 3.4–3.5 (2H,m), 4.44 (1H,d,J=12 Hz),4.67 (1H,d,J=12 Hz), 7.1–7.4 (9H, m)

MASS: 327 (M+Na)$^+$ (5) (2S,3S)-2-(benzyloxy)-5-(2-methoxyphenyl)pentan-3-ol was prepared from the compound obtained in Preparation 9.

NMR (CDCl$_3$, δ): 1.18 (3H, d,J=6 Hz), 1.6–1.9 (2H, m), 2.6–3.0 (3H,m), 3.4–3.5 (2H,m), 3.82 (3H,s), 4.44 (1H,d,J= 12 Hz),4.66 (1H,d,J=12 Hz), 6.8–7.0 (2H, m), 7.1–7.4 (7H,m)

MASS: 323 (M+Na)$^+$ (6) (2S,3S)-2-(benzyloxy)-5-(2-hexyloxyphenyl)pentan-3-ol was prepared from the compound obtained in Preparation 9.

NMR (CDCl$_3$, δ): 0.90 (3H,t,J=6 Hz), 1.18 (3H, d,J=6 Hz), 1.2–1.6 (6H,m), 1.6–1.9 (4H,m),2.66 (1H,d,J=3 Hz), 2.7–2.9 (2H,m), 3.4–3.5 (2H,m), 3.96 (2H,t,J=6 Hz), 4.44 (1H,d,J=11 Hz),4.66 (1H,d,J=11 Hz), 6.8–7.0 (2H, m), 7.1–7.3 (7H,m)

MASS: 393 (M+Na)$^+$ (7) (2S,3S)-2-(benzyloxy)-5-(2,3-dichlorophenyl)pentan-3-ol was prepared from the compound obtained in Preparation 9.

NMR (CDCl$_3$, δ): 1.19 (3H, d,J=5 Hz), 1.6–1.9 (2H, m), 2.65 (1H,d,J=3 Hz), 2.7–3.1 (2H,m), 3.3–3.5 (2H,m), 4.43 (1H,d,J=11 Hz),4.67 (1H,d,J=11 Hz), 7.0–7.5 (8H, m)

MASS: 361 (M+Na)$^+$ (8) (2S,3S)-2-(benzyloxy)-5-(2-phenethyloxyphenyl)pentan-3-ol was prepared from the compound obtained in Preparation 9.

NMR (CDCl$_3$, δ): 1.14 (3H, d,J=6 Hz), 1.6–1.8 (2H, m), 2.5–3.0 (3H,m), 3.10 (2H,t,J=7 Hz), 3.3–3.5 (2H,m), 4.18 (2H,t,J=7 Hz), 4.43 (1H,d,J=11 Hz), 4.65 (1H,d,J=11 Hz), 6.7–7.4 (14H,m)

MASS: 413 (M+Na)$^+$ (9) (2S,3S)-2-(benzyloxy)-5-(2,3-dimethylphenyl)pentan-3-ol was prepared from the compound obtained in Preparation 9.

NMR (CDCl$_3$,δ):1.19 (3H, d,J=6 Hz), 1.6–1.8 (2H, m), 2.22 (3H, s), 2.28 (3H, s), 2.6–3.0 (3H,m), 3.3–3.6 (2H,m), 4.43 (1H,d,J=11 Hz),4.67 (1H,d,J=11 Hz), 7.02 (3H,s), 7.2–7.4 (5H, m)

MASS: 321 (M+Na)$^+$

(10) (2S,3S)-2-(benzyloxy)-5-[2,3-(methylenedioxy) phenyl]-pentan-3-ol was prepared from the compound obtained in Preparation 9.

NMR (CDCl$_3$, δ): 1.19 (3H, d, J=6 Hz), 1.6–1.9 (2H, m), 2.6–2.9 (3H, m), 3.3–3.5 (2H, m), 4.43 (1H, d, J=12 Hz), 4.67 (1H, d, J=12 Hz), 5.92 (2H, s), 6.6–6.8 (3H, m), 7.33 (5H, s)

MS: 337 (M+Na)$^+$

Preparation 12

To a stirred solution of Pd(OAc)$_2$ (340 mg), nBu$_3$P (613 mg), and Et$_3$N (1.99 g) in DMF (30 ml) was added methyl 2-hydroxy-3-butenoate (1.76 g) followed by 1-iodonaphthalene (5.0 g), and the reaction mixture was stirred at 100° C. for 2.5 hours. The reaction mixture was poured into water (300 ml) and extracted with ethyl acetate. The organic layer was washed with brine, dried over magnesium sulfate, and evaporated in vacuo. The residue was purified by silica gel (130 g) column chromatography eluting with hexane/ethyl acetate (50:1) to give methyl 4-(1-naphthyl)-2-oxobutyrate (254 mg) as a red oil.

IR (neat): 3050, 2954, 1739, 1725 cm$^{-1}$

NMR (CDCl$_3$,δ): 3.25–3.55 (4H, m), 3.86 (3H, s), 7.25–8.10 (7H, m)

Preparation 13

NaBH$_4$ (22 mg) was added portionwise to an ice cooled solution of methyl 4-(1-naphthyl)-2-oxobutyrate (obtained in Preparation 12) (252.5 mg) in THF(5 ml)-H$_2$O (1 ml). After the addition was completed, the reaction mixture was stirred at ice-bath temperature for 30 minutes. Water (4 ml) was added, and the resulting mixture was stirred for several minutes and then extracted with ethyl acetate. The organic layer was washed with brine, dried over magnesium sulfate, and evaporated in vacuo. The residue was purified by silica gel (5 g) column chromatography eluting with hexane/ethyl acetate (10:1) to give methyl 2-hydroxy-4-(1-naphthyl) butyrate (84.4 mg) as a colorless oil.

IR (neat): 3700–3100, 3052, 2954, 1739, 1236, 1103 cm$^{-1}$

NMR (CDCl$_3$,δ): 2.03–2.31 (2H, m), 2.91 (1H, d, J=5.2 Hz), 3.23 (2H, t, J=7.9 Hz), 3.75 (3H, S), 4.29 (1H, m), 7.30–8.10 (7H, m)

MASS: 245 (M+H)$^+$

Preparation 14

NaBH$_4$ (1.82 g) was added portionwise to an ice cooled solution of ethyl (R)-2-hydroxy-4-phenylbutyrate (2.0 g) in methanol (40 ml). After the addition was completed, the reaction mixture was stirred at room temperature for 45 minutes. Water (20 ml) was added, and the resulting mixture was stirred for several minutes and then evaporated under reduced pressure. The residue was extracted with ethyl acetate. The extract was washed with brine and dried over magnesium sulfate. Evaporation of the solvent under reduced pressure gave (R)-4-phenylbutane-1,2-diol (1.63 g) as a colorless oil. This material was used for the next reaction without further purification.

Imidazole (1.96 g) was added to an ice cooled solution of the diol in DMF (20 ml) followed by tert-butyldimethylsilyl chloride (1.52 g). After 1 hour, the ice-bath was removed and then the mixture was stirred overnight at room temperature.

The reaction mixture was poured into water (200 ml) and extracted with ethyl acetate. The organic layer was washed with brine, dried over magnesium sulfate and evaporated in vacuo. The residue was purified by silica gel (50 g) column chromatography eluting with hexane/ethyl acetate (50:1) to give (R)-1-(tert-butyldimethylsilyloxy)-4-phenylbutan-2-ol (2.10 g) as a colorless oil.

IR (neat): 3800–3100, 2950, 2931, 2859, 1253, 1116, 1081 cm$^{-1}$

NMR (CDCl$_3$,δ): 0.52 (6H, s), 0.90 (9H, s), 1.60–1.85 (2H, m), 2.45 (1H, d, J=3.6 Hz), 2.60–2.95 (2H, m), 3.35–3.75 (3H, m), 7.15–7.35 (5H, m)

MASS: 281 (M+H)$^+$

Preparation 15

The following compounds were prepared by a similar procedure to that of Preparation 12.

(1) Methyl 4-(3-methylphenyl)-2-oxobutyrate was prepared as a pale yellow oil from 3-iodotoluene and methyl 2-hydroxy-3-butenoate.

IR (neat): 2954, 2923, 1731, 1238, 1074 cm$^{-1}$

NMR (CDCl$_3$, δ): 2.33 (3H, s), 2.92 (2H, t, J=7.5 Hz), 3.18 (2H, t, J=7.5 Hz), 3.86 (3H, s), 6.90–7.25 (4H, m)

(2) Methyl 4-[3-(trifluoromethyl)phenyl]-2-oxobutyrate was prepared as an oil from 3-iodobenzotrifluoride and methyl 2-hydroxy-3-butenoate.

IR (neat): 2958, 1739, 1728, 1241 cm$^{-1}$

NMR (CDCl$_3$, δ): 3.03 (2H, t, J=7.4 Hz), 3.22 (2H, t, J=7.4 Hz), 3.87 (3H, s), 7.35–7.55 (4H, m)

(3) Methyl 4-[3-(tert-butyldimethylsilyloxy)phenyl]-2-oxobutyrate was prepared as a yellow oil from 3-(tert-butyldimethylsilyloxy) iodobenzene and methyl 2-hydroxy-3-butenoate.

IR (neat): 2954, 2935, 2857, 1731, 1594, 1244 cm-1

NMR(CDCl$_3$, δ): 0.19 (6H, s), 0.98 (9H, s), 2.90 (2H, t, J=7.6 Hz), 3.16 (2H, t, J=7.6 Hz), 3.86 (3H, s), 6.65–6.85 (3H, m), 7.15 (1H, m)

MASS: 323 (M+H)$^+$

Preparation 16

The following compounds were prepared by a similar procedure to that of Preparation 13.

(1) Methyl 2-hydroxy-4-(3-methylphenyl)butyrate was prepared as a colorless oil from the compound obtained in Preparation 15(1).

IR (neat): 3700–3100, 3016, 2954, 2859, 1733, 1234, 1099 cm$^{-1}$

NMR (CDCl$_3$, δ): 1.80–2.20 (2H, m), 2.33 (3H, s), 2.65–2.85 (3H, m), 3.76 (3H, s), 4.20 (1H, m), 6.95–7.25 (4H, m)

MASS: 209 (M+H)$^+$ (2) Methyl 2-hydroxy-4-[3-(trifluoromethyl)phenyl]butyrate was prepared from the compound obtained in Preparation 15(2).

IR (neat): 3700–3200, 3016, 2956, 1739, 1328, 1122, 703 cm$^{-1}$

NMR (CDCl$_3$, δ): 1.85–2.25 (2H, m), 2.70–2.95 (3H, m), 3.76 (3H, s), 4.18 (1H, m), 7.35–7.55 (4H, m)

(3) Methyl 2-hydroxy-4-[3-(tert-butyldimethylsilyloxy)-phenyl]butyrate was prepared as a colorless oil from the compound obtained in Preparation 15(3).

IR (neat): 3700–3100, 2954, 2857, 1739, 1595, 1479, 1444, 1273 cm$^{-1}$

NMR (CDCl$_3$, δ): 0.19 (6H, s), 0.98 (9H, s), 1.80–2.20 (2H, m), 2.65–2.80 (3H, m), 3.77 (3H, s), 4.18 (1H, m), 6.65–6.90 (3H, m), 7.13 (1H, m)

MASS: 325 (M+H)$^+$

Preparation 17

The following compounds were prepared by a similar procedure to that of Preparation 2.

(1) Methyl 2-(4-carbamoyl-1-imidazolyl)-4-(1-naphthyl) butyrate was prepared from the compound obtained in Preparation 1 and the compound obtained in Preparation 13.

IR (KBr): 3343, 3185, 1745, 1662 cm$^{-1}$

NMR (CDCl$_3$,δ) 2.40–3.25 (4H, m), 3.73 (3H, m), 4.71 (1H, m), 5.42 (1H, brs), 6.98 (1H, brs), 7.19 (1H, d, J=6.9 Hz), 7.35–7.60 (4H, m), 7.74–7.95 (4H, m)

MASS: 338 (M+H)$^+$ (2) Methyl 2-(4-carbamoyl-1-imidazolyl)-4-(3-methylphenyl)-butyrate was prepared from the compound obtained in Preparation 1 and the compound obtained in Preparation 16(1).

IR (neat): 3800–2800, 1745, 1658 cm$^{-1}$

NMR (CDCl$_3$, δ): 2.25–2.75 (7H, m), 3.75 (3H, s), 4.64 (1H, m), 5.43 (1H, br s), 6.85–7.25 (5H, m), 7.45 (1H, s), 7.71 (1H, s)

MASS: 302 (M+H)$^+$ (3) Methyl 2-(4-carbamoyl-1-imidazolyl)-4-[3-(trifluoromethyl)-phenyl]butyrate was prepared from the compound obtained in Preparation 1 and the compound obtained in Preparation 16(2).

IR (neat): 3700–2800, 1743, 1236 cm$^{-1}$

NMR (CDCl$_3$, δ): 2.25–2.80 (4H, m), 3.77 (3H, m), 4.65 (1H, m), 5.43 (1H, br s), 6.96 (1H, br s), 7.20–7.55 (5H, m), 7.73 (1H, s)

MASS: 356 (M+H)$^+$ (4) Methyl 2-(4-carbamoyl-1-imidazolyl)-4-(3-hydroxyphenyl)-butyrate was prepared from the compound obtained in Preparation 1 and the compound obtained in Preparation 16(3).

IR (neat): 3700–2800, 1745, 1664, 1590, 1267, 1234 cm$^{-1}$

NMR (CDCl$_3$, δ): 2.20–2.80 (4H, m), 3.76 (3H, s), 4.65 (1H, m), 5.64 (1H, br s), 6.50–6.85 (3H, m), 6.90–7.30 (2H, m), 7.55 (1H, s), 7.73 (1H, s)

MASS: 304 (M+H)$^+$

Preparation 18

To a stirred solution of Pd (OAc)$_2$ (40 mg, 0.18 mmol), nBu$_3$P (71 mg, 0.35 mmol), and Et$_3$N (232 mg, 2.29 mmol) in DMF (5 ml) was added 3-butene-1,2-diol (155 mg, 1.76 mmol) followed by 4-iodotoluene (500 mg, 2.29 mmol), and the reaction mixture was stirred at 100° C. for 1.5 h. The reaction mixture was poured into water (50 ml) and extracted with ethyl acetate. The organic layer was washed with brine, dried (magnesium sulfate) and evaporated in vacuo. The residue was purified by silica gel (10 g) column chromatography eluting with toluene/ethyl acetate (50:1) to give 1-hydroxy-4-(p-tolyl)butan-2-one (230 mg, 73.4%) as a pale yellow solid.

To an ice cooled solution of 1-hydroxy-4-(p-tolyl)butan-2-one in DMF (5 ml) was added imidazole (264 mg, 3.88 mmol) followed by tert-butyldimethylsilyl chloride (234 mg, 1.55 mmol). After 30 minutes the ice-bath was removed and then the mixture was stirred overnight at room temperature. The reaction mixture was poured into water (50 ml) and extracted with ethyl acetate. The organic layer was washed with brine, dried (magnesium sulfate), and concentrated in vacuo. The residue was purified by silica gel (8 g) column chromatography eluting with hexane/ethyl acetate (50:1) to give 1-(tert-butyldimethylsilyloxy)-4-(4-methylphenyl) butan-2-one (350 mg, 67.9%) as a colorless oil.

IR (neat): 2933, 2857, 1726, 1255, 1105, 842 cm$^{-1}$

NMR (CDCl$_3$, δ): 0.07 (6H, s), 0.91 (9H, s), 2.31 (3H, s), 2.75–2.95 (4H, m), 4.14 (2H, s), 7.08 (4H, s)

Preparation 19

1-(Tert-butyldimethylsilyloxy)-4-[3-(ethoxycarbonyl)-phenyl]butan-2-one (1.62 g, 42.7%) was prepared as a colorless oil by a similar procedure to that of Preparation 18 from ethyl 3-iodobenzoate and 3-butene-1,2-diol.

IR (neat): 2929, 2858, 1720, 1238, 1103 cm$^{-1}$

NMR(CDCl$_3$,δ): 0.07(6H,s), 0.91(9H,s), 1.40 (3H, t, J=7.1 Hz), 2.75–3.05 (4H, m), 4.15 (2H, s), 4.37 (2H, q, J=7.1 Hz), 7.30–7.45 (2H, m), 7.85–7.95 (2H, m)

MASS: 351 (M+H)$^+$

Preparation 20

To a stirred solution of Pd (OAc)$_2$ (75 mg, 0.34 mmol), nBu$_3$P (136 mg, 0.67 mmol), and Et$_3$N (442 mg, 4.37 mmol) in DMF (10 ml) was added 3-butene-1,2-diol (296 mg, 3.36 mmol) followed by methyl 3-bromophenylacetate (1.0 g, 4.37 mmol), and the reaction mixture was stirred at 100° C. for 5 h. The reaction mixture was poured into water (100 ml) and extracted with ethyl acetate. The organic layer was washed with brine, dried (magnesium sulfate) and evaporated in vacuo. The residue was purified by silica gel (25 g) column chromatography eluting with toluene/ethyl acetate (20:1) to give methyl 3-(4-hydroxy-3-oxobutyl) phenylacetate (193 mg, 24.4%) as an oil.

IR (neat): 3700–3100, 2950, 1732, 1261, 1159, 1069 cm$^{-1}$

NMR (CDCl$_3$, δ): 2.73 (2H, t, J=7.5 Hz), 2.96 (2H, t, J=7.5 Hz), 3.06 (1H, t, J=4.8 Hz), 3.60 (2H, s), 3.70 (3H, s), 4.19 (2H, d, J=4.8 Hz), 7.05–7.35 (4H, m)

MASS: 237 (M+H)$^+$

Preparation 21

The following compounds were prepared by a similar procedure to that of Preparation 13.

(1) 1-(tert-Butyldimethylsilyloxy)-4-(4-methylphenyl) butan-2-ol was prepared as a colorless oil from the compound obtained in Preparation 18.

IR (neat): 3442, 2931, 2859, 1463, 1254, 1116 cm$^{-1}$

NMR (CDCl$_3$, δ): 0.06 (6H, s), 0.90 (9H, s), 1.60–1.85 (2H, m), 2.32 (3H, s), 2.44 (1H, d, J=3.5 Hz), 2.55–2.90 (2H, m), 3.30–3.80 (3H, m), 7.10 (4H, s)

MASS: 295 (M+H)$^+$ (2) 1-(tert-Butyldimethylsilyloxy)-4-[3-(ethoxycarbonyl) phenyl]-butan-2-ol was prepared as a colorless oil from the compound obtained in Preparation 19.

IR (neat): 3700–3100, 2933, 2860, 1718, 1279, 1110 cm$^{-1}$

NMR(CDCl$_3$,δ):0.07 (6H, s), 0.90 (9H, s), 1.40 (3H, t, J=7.1 Hz), 1.65–1.85 (2H, m), 2.46 (1H, d, J=3.4 Hz), 2.65–3.00 (2H, m), 3.35–3.75 (3H, m), 4.37 (2H, q, J=7.1 Hz), 7.30–7.45 (2H, m), 7.80–7.95 (2H, m)

MASS: 353 (M+H)$^+$ (3) Methyl 3-[4-(tert-butyldimethylsilyloxy)-3-hydroxybutyl]-phenylacetate was prepared as a colorless oil from the compound obtained in Preparation 22.

IR (neat): 3800–3100, 2931, 2858, 1741, 1250, 1119 cm$^{-1}$

NMR (CDCl$_3$, δ): 0.07 (6H, s), 0.90 (9H, s), 1.60–1.80 (2H, m), 2.45 (1H, d, J=3.6 Hz), 2.55–2.95 (2H, m), 3.35–3.75 (8H, m), 7.05–7.35 (4H, m)

MASS: 353 (M+H)$^+$

Preparation 22

To an ice cooled solution of methyl 3-(4-hydroxy-3-oxobutyl)phenylacetate (472 mg, 2.00 mmol) in DMF (10 ml) was added imidazole (264 mg, 3.88 mmol) followed by tert-butyldimethylsilyl chloride (408 mg, 5.99 mmol). After 30 minutes the ice-bath was removed and then the mixture was stirred overnight at room temperature. The reaction mixture was poured into water (100 ml) and extracted with ethyl acetate. The organic layer was washed with brine, dried (magnesium sulfate), and concentrated in vacuo. The residue was purified by silica gel (20 g) column chromatography eluting with hexane/ethyl acetate (10:1) to give methyl 3-[4-(tert-butyldimethylsilyloxy)-3-oxobutyl] phenylacetate (664 mg, 94.9%) as a colorless oil.

IR (neat): 2952, 2933, 2856, 1738, 1250, 1153, 1101 cm$^{-1}$

NMR (CDCl$_3$, δ): 0.07 (6H, s), 0.91 (9H, s), 2.75–3.00 (4H, m), 3.60 (2H, s), 3.69 (3H, s), 4.15 (2H, s), 7.05–7.30 (4H, m)

MASS: 351 (M+H)$^+$

Preparation 23

A solution of ethyl 2-(4-carbamoyl-1-imidazolyl)-4-phenyl-butyrate (obtained in Preparation 2) in DMF (5 ml) was added to an ice-cooled solution of POCl$_3$ (0.71 ml) in DMF (6 ml) under nitrogen atmosphere. After 1.5 h, the solvent was poured into water (50 ml) and the solution was neutralized with saturated NaHCO$_3$aq. The resulting mixture was extracted with ethyl acetate. The organic layer was washed with brine, dried over sodium sulfate, and concentrated in vacuo. The residue was purified by silica gel (16 g) column chromatography eluting with chloroform/methanol (100:1) to give ethyl 2-(4-cyano-1-imidazolyl)-4-phenylbutyrate (435 mg, 101.2%).

IR (neat): 3132, 2978, 2933, 2235, 1741, 1236, 1157 cm$^{-1}$

NMR (CDCl$_3$, δ): 1.28 (3H, t, J=7.1 Hz), 2.20–2.80 (4H, m), 4.23 (2H, q, J=7.1 Hz), 4.63 (1H, m), 7.00–7.40 (5H, m), 7.53 (1H, s), 7.58 (1H, s)

MASS: 284 (M+H)$^+$

Preparation 24

1-(tert-Butyldimethylsilyloxy)-3-phenoxypropan-2-ol was prepared from 3-phenoxy-1,2-propanediol and tert-butyldimethylsilyl chloride by a similar procedure to that of Preparation 22.

IR (neat): 3700–3100, 2931, 2860, 1244, 1092 cm$^{-1}$

NMR (CDCl$_3$, δ): 0.08 (6H, s) , 0.90 (9H, s) , 2.54 (1H, d, J=5.4 Hz), 3.75–4.15 (5H, m), 6.85–7.05 (3H, m), 7.25–7.35 (2H, m)

MASS: 283 (M+H)$^+$

Preparation 25

1-Naphthylmethylmagnesium chloride was prepared from magnesium turnings (2.88 g) and 1-(chloromethyl) naphthalene (6.98 g) in ether (80 ml) by the method of J. Am. Chem. Soc. (1943) 65, 295. A solution of lithium chloride (167 mg) and copper (II) chloride (266 mg) in THF (10 ml) was added dropwise to the ethereal solution of the Grignard reagent followed by addition of a solution of (2RS,3S)-3-(benzyloxy)-1,2-epoxybutane (3.52 g) in ether (30 ml) below −70° C. The mixture was stirred at −78° C. for 1 h, and then allowed to warm to room temperature and stirred overnight. After cooling, the mixture was quenched with saturated aqueous ammonium chloride solution (100 ml). The insoluble material was filtered through Celite and the filter cake was washed with ether. The filtrate and washings were combined, and the organic layer was washed with water and brine, dried over anhydrous magnesium sulfate and concentrated in vacuo to give an oil. Flash chromatography (hexane:ethyl acetate=9:1→4:1) gave (2S, 3S)-2-benzyloxy-5-(1-naphthyl)pentan-3-ol (2.66 g, 42.0%) as the first eluate and (2S,3R)-2-benzyloxy-5-(1-naphthyl) pentan-3-ol (1.36 g, 21.5%) as the second eluate.

(2S,3S)-2-benzyloxy-5-(1-naphthyl)pentan-3-ol

IR (neat): 3558, 3458, 2870, 1078 cm$^{-1}$

NMR (CDCl$_3$, d): 1.17 (3H, d, J=6.0 Hz), 1.89 (2H, m), 2.70 (1H, d, J=4.0 Hz), 3.15 (1H, m), 3.30–3.60 (3H, m), 4.43 (1H, d, J=11.4 Hz), 4.67 (1H, d, J=11.4 Hz), 7.20–8.15 (12H, m)

[α]$_D^{26}$ −27.8° (c 0.5, EtOH)

(2S,3R)-2-benzyloxy-5-(1-naphthyl)pentan-3-ol

IR (neat): 3556, 3458, 2871, 1088 cm$^{-1}$

NMR (CDCl$_3$, d): 1.16 (3H, d, J=6.3 Hz), 1.86 (2H, m), 2.19 (1H, d, J=4.0 Hz), 3.11 (1H, m), 3.32–3.55 (2H, m), 3.87 (1H, m), 4.47 (1H, d, J=11.8 Hz), 4.60 (1H, d, J=11.8 Hz), 7.19–8.06 (12H, m)

[α]$_D^{26}$+33.5° (c 0.5, EtOH)

Preparation 26

A solution of (S)-2-(benzyloxy)propanal (Bull. Chem. Soc. Jpn. (1989) 62, 3038, 16.25 g) in ether (200 ml) was added to a suspension of zinc bromide (26.75 g) in ether (50 ml) below 6° C. and then an ethereal solution of 2-(1-naphthyl)ethylmagnasium bromide, prepared from 2-(1-naphthyl)ethyl bromide (46.55 g) and magnesium turnings (9.63 g) in ether (300 ml), was added below 8° C. The mixture was stirred at 4° C. for 1 h and then THF (200 ml) was added. The final mixture was stirred overnight at room temperature. After cooling, the mixture was quenched with saturated aqueous ammonium chloride solution (200 ml) and insoluble material was filtered. The filtrate was extracted with ethyl acetate and the extract was washed with brine, dried and concentrated in vacuo. Flash chromatography (hexane:ethyl acetate =9:1) gave (2S,3S)-2-benzyloxy-5-(1-naphthyl)pentan-3-ol (9.78 g, 30.8%) as an oil.

Preparation 27

To an ice-cooled solution of (2S,3S)-2-benzyloxy-5-(1-naphthyl)pentan-3-ol (obtained in Preparation 26) (7.43 g) in dichloromethane (100 ml) was added methanesulfonyl chloride (2.15 ml) followed by triethylamine (3.88 ml). The mixture was stirred at 4° C. for 40 min. After being diluted with dichloromethane, the mixture was washed with water and brine, dried and concentrated in vacuo to give (2S,3S)-2-benzyloxy-5-(1-naphthyl)-3-pentyl methanesulfonate (9.92 g, 107.4%) as an oil. The product was used directly in the next step without further purification.

IR (neat): 1344, 1173 cm$^{-1}$

NMR (CDCl$_3$, d): 1.23 (3H, d, J=6.4 Hz), 2.04–2.25 (2H, m), 2.98 (3H, s), 3.06–3.33 (2H, m), 3.82 (1H, m), 4.44 (1H, d, J=11.5 Hz), 4.64 (1H, d, J=11.5 Hz), 4.80 (1H, m), 7.25–8.02 (12H, m)

Preparation 28

The following compound was prepared by a similar procedure to that of Preparation 25.

(1) (2S,3S)-2-(benzyloxy)-5-[2-(trifluoromethyl)phenyl]pentan-3-ol was prepared from (S)-2-(benzyloxy)propanal.

NMR (CDCl$_3$, δ): 1.19 (3H, d,J=6 Hz), 1.6–1.9 (2H, m), 2.67 (1H,d,J=3 Hz), 2.7–3.2 (2H,m), 3.3–3.6 (2H,m), 4.44 (1H,d,J=11 Hz),4.67 (1H,d,J=11 Hz), 7.2–7.7 (9H, m)

MASS: 361 (M+Na)$^+$ (2) (2S,3S)-2-(tert-butyldimethylsilyloxy)-5-phenyl-pentan-3-ol was prepared from (S)-2-(tert-butyldimethylsilyloxy) propanal (Synthesis 1996, 652, 3.00 g) and 2-phenylethyl bromide.

IR (neat): 3573,3473,2935,1078 cm$^{-1}$

NMR (CDCl$_3$, d): 0.09 (6H, s), 0.90 (9H, s), 1.13 (3H, d, J=6.2 Hz), 1.66–1.77 (2H, m), 2.42 (1H, d, J=5.3 Hz), 2.60–2.95 (2H, m), 3.30 (1H, m), 3.65 (1H, m), 7.14–7.32 (5H, m)

MS (ESI, m/z): 317(M+Na)$^+$

[α]$_D^{27}$−31.6° (c 0.5, EtOH)

(3) (2S,3S)-2-(tert-dimethylsilyloxy)-5-[2-(benzyloxy)phenyl]-pentan-3-ol was prepared from (S)-2-(tert-butyldimethyl-silyloxy)propanal.

NMR (CDCl$_3$, δ): 0.05 (3H, s), 0.06 (3H, s), 0.88 (9H, s), 1.08 (3H, d, J=6 Hz), 1.6–1.9 (2H, m), 2.40 (1H, d, J=5 Hz), 2.6–3.0 (2H, m), 3.2–3.4 (1H, m), 3.6–3.7 (1H, m), 5.09 (2H, s), 6.8–7.5 (9H, m)

MS: 423 (M+Na)$^+$ (4) (2S,3S)-2-(benzyloxy)-5-(2-naphthyl)pentan-3-ol was prepared from (S)-2-(benzyloxy)propanal.

IR (neat): 3442, 1078 cm$^{-1}$

NMR (CDCl$_3$, δ): 1.18 (3H, d, J=6 Hz), 1.7–2.0 (2H, m), 2.64 (1H, d, J=3 Hz), 2.7–3.1 (2H, m), 3.3–3.6 (2H, m), 4.43 (1H, d, J=11 Hz),4.67 (1H, d, J=11 Hz), 7.2–7.6 (8H, m), 7.64 (1H, s), 7.6–7.9 (3H, m)

MS: 343 (M+Na)$^+$ (5) (2S,3S)-2-(benzyloxy)-6-(1-naphthyl)hexan-3-ol was prepared from (S)-2-(benzyloxy)propanal.

IR (neat): 3437, 1081 cm$^{-}$

NMR (CDCl$_3$, δ): 1.18 (3H, d, J=6 Hz), 1.5–1.7 (2H, m), 1.7– 2.2 (2H, m), 2.59 (1H, d, J=4 Hz), 3.0–3.2 (2H, m), 3.3–3.6 (2H,m), 4.41 (1H, d, J=11 Hz), 4.66 (1H, d, J=11 Hz), 7.2–7.6 (9H, m), 7.70 (1H, d, J=8 Hz), 7.7–8.1 (2H, m)

MS: 357 (M+Na)$^+$

Preparation 29

The following compounds were prepared according to the procedure of Preparation 27.

(1) (2S,3R)-2-Benzyloxy-5-(1-naphthyl)-3-pentyl methane-sulfonate was prepared from (2S,3R)-2-benzyloxy-5-(1-naphthyl)pentan-3-ol obtained in Preparation 25.

IR (neat): 1346, 1171 cm$^{-1}$

NMR (CDCl$_3$, d): 1.23 (3H, d, J=6.4 Hz), 1.80–2.25 (2H, m), 3.08 (3H, s), 3.10 (1H, m), 3.40 (1H, m), 3.64 (1H, m), 4.58 (2H, s), 5.04 (1H, m), 7.30–8.05 (12H, m)

(2) (2S,3S)-2-(tert-Butyldimethylsilyloxy)-5-phenyl-3-pentyl methanesulfonate was prepared from (2S,3S)-2-(tert-butyldimethylsilyloxy)-5-phenyl-pentan-3-ol (obtained in Preparation 28(2)).

IR (neat): 2935, 1352, 1174 cm$^{-1}$

NMR (CDCl$_3$, d): 0.03 (3H, s), 0.06 (3H, s), 0.86 (9H, s), 1.17 (3H, d, J=6.2 Hz), 1.80–2.20 (2H, m), 2.60–2.90 (2H, m), 3.01 (3H, s), 4.10 (1H, m), 4.53 (1H, m), 7.10–7.40 (5H, m)

EXAMPLE 1

NaBH$_4$ (491 mg) was added portionwise to an ice cooled solution of ethyl 2-(4-carbamoyl-1-imidazolyl)-4-phenylbutyrate (obtained in Preparation 2) (391 mg) in methanol (20 ml) under an nitrogen atmosphere. After the addition was completed, the reaction mixture was stirred at room temperature for 30 minutes. Water was added, and the resulting mixture was stirred for several minutes and then evaporated under reduced pressure. The residue was partitioned between chloroform and water. The organic layer was washed with brine and dried over sodium sulfate. Evaporation of the solvent under reduced pressure gave 1-(1-hydroxy-4-phenyl-2-butyl)imidazole-4-carboxamide (347 mg) as a white solid.

mp: 127.0–129.5° C.

IR (KBr): 3500–2700, 1664 cm$^{-1}$

NMR (DMSO-d$_6$,δ): 2.06 (2H, q, J=7.6 Hz), 2.39 (2H, t, J=7.6 Hz), 3.63 (2H, t, J=5.5 Hz), 4.10 (1H, qui, J=6.4 Hz), 5.01 (1H, t, J=5.3 Hz), 7.04 (1H, br s), 7.10–7.33 (6H, m), 7.70 (1H, s), 7.75 (1H, s)

MASS: 260 (M+H)$^+$

EXAMPLE 2

The following compounds were obtained according to the similar manner to that of Example 1.

(1) 1-(2-Hydroxy-1-phenylethyl)imidazole-4-carboxamide was prepared from the compound obtained in Preparation 4(1).

mp: 147–149° C.

IR (KBr): 3324, 3187, 1668 cm$^{-1}$

NMR (CDCl$_3$,δ): 4.26 (2H, d, J=5.4 Hz), 5.35 (2H, br), 7.05 (1H, br), 7.10–7.50 (5H, m), 7.64 (1H, s), 7.75 (1H, s)

MASS: 232 (M+H)$^+$ (2) 1-(1-Hydroxy-2-octyl)imidazole-4-carboxamide was prepared from the compound obtained in Preparation 4(2).

mp: 97.5–100.5° C.

IR (KBr): 3324, 3178, 2927, 2857, 1662 cm$^{-1}$

NMR (CDCl$_3$,δ): 0.83 (3H, t, J=6.5 Hz), 0.90–1.35 (8H, m), 1.60–1.80 (2H, m), 3.60 (2H, t, J=5.6 Hz), 4.09 (1H, qui, J=6.5 Hz), 4.98 (1H, t, J=5.3 Hz), 7.00 (1H, s), 7.22 (1H, s), 7.67 (2H, s)

MASS: 240 (M+H)$^+$ (3) 1-(1-Hydroxy-2-pentyl)imidazole-4-carboxamide was prepared from the compound obtained in Preparation 5.

mp: 160° C.

IR (KBr): 3336, 3172, 1654 cm$^{-1}$

NMR (DMSO-d$_6$,δ): 0.84 (3H, t, J=7.2 Hz), 1.10 (2H, m), 1.70 (2H, q, J=7.5 Hz), 3.61 (2H, t, J=5.4 Hz), 4.12 (1H, qui, J=6.5 Hz), 4.99 (1H, t, J=5.4 Hz), 7.01 (1H, s), 7.24 (1H, s), 7.69 (2H, s)

MASS: 198 (M+H)$^+$ (4) 1-(1,4-Dihydroxy-2-butyl)imidazole-4-carboxamide was prepared from the compound obtained in Preparation 6.

IR (KBr): 3700–3100, 1670 cm$^{-1}$

NMR (DMSO-d$_6$,δ): 1.86 (2H, m), 3.10–3.45 (2H, m), 3.62 (2H, t, J=5.5 Hz), 4.29 (1H, m), 4.60 (1H, t, J=5.0 Hz), 5.01 (1H, t, J=5.3 Hz), 7.02 (1H, s), 7.25 (1H, s), 7.65 (1H, s), 7.68 (1H, S)

MASS: 200 (M+H)$^+$ (5) 1-[1-hydroxy-4-(1-naphthyl)-2-butyl]imidazole-4-carboxamide was prepared from the compound obtained in Preparation 17(1).

mp: 138–140° C.

IR (KBr): 3600–2800, 1660, 1598 cm$^{-1}$ (M+H)$^+$

NMR (DMSO-d$_6$,δ): 2.17 (2H, t, J=7.7 Hz), 2.70–3.10 (2H, m), 3.68 (2H, t, J=5.4 Hz), 4.27 (1H, m), 5.04 (1H, t, J=5.3 Hz), 7.06 (1H, brs), 7.20–7.60 (5H, m), 7.75–8.00 (5H, m)

MASS: 310 (M+H)$^+$ (6) 1-[1-Hydroxy-4-(3-methylphenyl)-2-butyl]imidazole-4-carboxamide was obtained as a white solid from the compound obtained in Preparation 17(2).

mp: 115.5–117.5° C.

IR (KBr): 3325, 3195, 3110, 2935, 2854, 1662, 1604 cm$^{-1}$

NMR (DMSO-d$_6$, δ): 1.90–2.50 (7H, m), 3.62 (2H, m), 4.10 (1H, m), 5.01 (1H, br), 6.85–7.40 (6H, m), 7.70 (1H, s), 7.74 (1H, s)

MASS: 274 (M+H)$^+$ (7) 1-{1-Hydroxy-4-[3-(trifluoromethyl)phenyl]-2-butyl}-imidazole-4-carboxamide was obtained as a white solid from the compound obtained in Preparation 17(3).

mp: 103–106° C.

IR (KBr): 3332, 3195, 3143, 1670, 1335 cm$^{-1}$

NMR (DMSO-d$_6$, δ): 2.11 (2H, q, J=8.0 Hz), 2.35–2.75 (2H, m), 3.64 (2H, m), 4.13 (1H, m), 5.03 (1H, br s), 7.03 (1H, br s), 7.26 (1H, br s), 7.40–7.65 (4H, m), 7.71 (1H, s), 7.77 (1H, s)

MASS: 328 (M+H)$^+$ (8) 1-[1-Hydroxy-4-(3-hydroxyphenyl)-2-butyl]imidazole-4-carboxamide was obtained from the compound obtained in Preparation 17(4).

IR (KBr): 3700–2800, 1658, 1600 cm$^{-1}$

NMR (DMSO-d$_6$, δ): 1.90–2.50 (4H, m), 3.62 (2H, m), 4.14 (1H, m), 5.09 (1H, t, J=5.3 Hz), 6.45–6.65 (3H, m), 6.95–7.60 (4H, m), 7.74 (1H, s), 7.80 (1H, s), 9.37 (1H, s)

MASS: 276 (M+H)$^+$

EXAMPLE 3

The following compounds were obtained according to a similar manner to that of Preparation 2.

(1) 1-[(2S)-2-(Benzyloxy)-5-phenyl-3-pentyl]imidazole-4-carboxamide was prepared from the compound obtained in Preparation 1 and the compound obtained in Preparation 10.

IR (neat): 3700–2800, 1673, 1658 cm$^{-1}$

NMR (CDCl$_3$,δ): 0.98–1.08 (3H, m), 2.10–2.75 (4H, m), 3.60–4.00 (2H, m), 4.05–4.70 (2H, m), 5.39 (1H, brs), 6.90–7.10 (3H, m), 7.15–7.45 (9H, m), 7.67 (1H, dd, J=6.1, 1.3 Hz)

MASS: 364 (M+H)$^+$, 386 (M+Na)$^+$ (2) 1-[(2S)-2-(Benzyloxy)-6-phenyl-3-hexyl]imidazole-4-carboxamide was prepared from the compound obtained in Preparation 1 and the compound obtained in Preparation 11(1).

IR (neat): 3500–2800, 1666, 1589, 1236, 1095 cm$^{-1}$

NMR (CDCl$_3$,δ): 0.98–1.08 (3H, m), 1.30–2.20 (4H, m), 2.30–3.20 (2H, m), 3.50–4.10 (2H, m), 4.20–4.65 (2H, m), 5.37(1H, br s), 6.95(1H, brs), 7.00–7.80 (12H, m)

MASS: 378 (M+H)$^+$ (3) 1-[(2S)-2-(Benzyloxy)-5-(1-naphthyl)-3-pentyl]imidazole-4-carboxamide was prepared from the compound obtained in Preparation 1 and the compound obtained in Preparation 11(2).

IR (neat): 3700–2800, 1666, 1594, 1236, 1097 cm$^{-1}$

NMR (CDCl$_3$, δ): 1.04 (3H, d, J=6.2 Hz), 2.10–2.60 (2H, m), 2.70–3.15 (2H, m), 3.50–4.10 (2H, m), 4.20–4.65 (2H, m), 5.41 (1H, brs), 7.01 (1H, brs), 7.10–7.60 (9H, m), 7.65–7.95 (5H, m)

MASS: 414 (M+H)$^+$ (4) 1-[1-(tert-Butyldimethylsilyloxy)-4-(4-methylphenyl)-2-butyl]imidazole-4-carboxamide was prepared from the compound obtained Preparation 1 and the compound obtained in Preparation 21(1).

NMR (CDCl$_3$, δ): −0.07 (3H, s), −0.05 (3H, s), 0.84 (9H, s), 1.95–2.25 (2H, m), 2.32 (3H, s), 2.35–2.80 (2H, m), 3.65–4.10 (3H, m), 5.40 (1H, br s), 6.90–7.15 (5H, m), 7.44 (1H, s), 7.64 (1H, s)

MASS: 388 (M+H)$^+$ (5) 1-{1-(tert-Butyldimethylsilyloxy)-4-[3-(ethoxycarbonyl)-phenyl]-2-butyl}imidazole-4-carboxamide was prepared from the compound obtained in Preparation 1 and the compound obtained in Preparation 21(2).

IR (neat): 3700–3050, 2931, 2860, 1716, 1666, 1595, 1240, 1095 cm$^{-1}$

NMR (CDCl$_3$, δ): −0.06 (3H, s), −0.04 (3H, s), 0.83 (9H, s), 1.41 (3H, t, J=7.1 Hz), 2.18 (2H, m), 2.40–2.80 (2H, m), 3.60–4.10(3H,m),3.65–4.10(3H,m),4.39(2H, q, J=7.1 Hz), 5.37 (1H, br s), 6.95 (1H, br s), 7.20–7.42 (2H, m), 7.45 (1H, s), 7.65 (1H, s), 7.75–7.95 (2H, m)

MASS: 446 (M+H)$^+$ (6) 1-{1-(tert-Butyldimethylsilyloxy)-4-{3-[(methoxycarbonyl)-methyl]phenyl}-2-butyl}imidazole-4-carboxamide was prepared from the compound obtained in Preparation 1 and the compound obtained in Preparation 21(3).

IR (neat): 3800–3000, 2952, 2858, 1739, 1676, 1257, 1126 cm$^{-1}$

NMR (CDCl$_3$, δ): −0.07 (3H, s), −0.04 (3H, s), 0.83 (9H, s), 2.05–2.25 (2H, m), 2.30–2.75 (2H, m), 3.60 (2H, s), 3.70–3.85 (5H, m), 3.98 (1H, m), 5.39 (1H, br s), 6.90–7.35 (5H, m), 7.46 (1H, s), 7.65 (1H, s)

MASS: 446 (M+H)$^+$ (7) 1-(1-Hydroxy-3-phenoxy-2-propyl)imidazole-4-carboxamide was prepared from the compound obtained in Preparation 1 and the compound obtained in Preparation 24.

mp: 147.5–149.5° C.

IR (KBr): 3330, 3188, 1662, 1600, 1246 cm$^{-1}$

NMR (DMSO-d$_6$, δ): 3.80–4.30 (5H, m), 5.53 (1H, d, J=4.1 Hz), 6.85–7.10 (4H, m), 7.20–7.40 (3H, m), 7.63 (2H, s)

MASS: 262 (M+H)$^+$ (8) 1-[(2S,3R)-2-(benzyloxy)-5-(2-methylphenyl)-3-pentyl]-imidazole-4-carboxamide was prepared from the compound obtained in Preparation 1 and the compound obtained in Preparation 11(3).

NMR (CDCl$_3$,δ): 1.07 (3H,d,J=6 Hz), 2.0–2.6 (4H,m), 2.18 (3H,s), 3.6–3.8 (1H,m), 3.9–4.1 (1H,m), 4.38 (1H,d,J=11 Hz), 4.58 (1H,d,J=11 Hz), 5.39 (1H,s), 6.9–7.4 (10H,m), 7.45 (1H,d,J=1 Hz), 7.67 (1H,d,J=1 Hz)

MASS: 378 (M+H)$^+$ (9) 1-[(2S,3R)-2-(benzyloxy)-5-(2-chlorophenyl)-3-pentyl]-imidazole-4-carboxamide was prepared from the compound obtained in Preparation 1 and the compound obtained in Preparation 11(4).

NMR (CDCl$_3$, δ): 1.08 (3H,d,J=6 Hz), 2.0–2.5 (2H,m), 2.5–2.7 (2H,m), 3.6–3.7 (1H,m), 3.9–4.1 (1H,m), 4.38 (1H, d,J=12 Hz), 4.58 (1H,d,J=12 Hz), 5.37 (1H,s), 6.9–7.4 (10H,m), 7.48 (1H,d,J=1Hz), 7.67 (1H,d,J=1 Hz)

MASS: 420 (M+Na)$^+$

(10) 1-[(2S,3R)-2-(benzyloxy)-5-(2-methoxyphenyl)-3-pentyl]-imidazole-4-carboxamide was prepared from the compound obtained in Preparation 1 and the compound obtained in Preparation 11(5).

NMR (CDCl$_3$, δ): 1.04 (3H,d,J=6 Hz), 2.0–2.6 (4H,m), 3.6–3.7 (1H,m), 3.80 (3H,s), 3.9–4.1 (1H,m), 4.39 (1H,d,J=12 Hz), 4.57 (1H,d,J=12 Hz), 5.38 (1H,s), 6.8–7.4 (10H,m), 7.45 (1H,d,J=1 Hz), 7.69 (1H,d,J=1Hz)

MASS: 394 (M+H)$^+$

(11) 1-[(2S,3R)-2-(benzyloxy)-5-(2-hexyloxyphenyl)-3-pentyl]-imidazole-4-carboxamide was prepared from the compound obtained in Preparation 1 and the compound obtained in Preparation 11(6).

NMR (CDCl$_3$, δ): 0.8–1.0 (3H,m), 1.05 (3H,d,J=6 Hz), 1.2–1.5 (6H,m), 1.6–1.9 (2H,m), 2.0–2.6 (4H,m), 3.6–3.7 (1H,m), 3.8–4.0 (3H,m), 4.38 (1H,d,J=12 Hz), 4.56 (1H,d, J=12 Hz), 5.37 (1H,s), 6.8–7.4 (10H,m), 7.44 (1H,s), 7.67 (1H,s)

MASS: 464 (M+H)$^+$

(12) 1-[(2S,3R)-2-(benzyloxy)-5-(2,3-dichlorophenyl)-3-pentyl]-imidazole-4-carboxamide was prepared from the compound obtained in Preparation 1 and the compound obtained in Preparation 11(7).

NMR (CDCl$_3$, δ): 1.08 (3H,d,J=6 Hz), 2.0–2.5 (2H,m), 2.5–2.7 (2H,m), 3.6–4.1 (2H,m), 4.38 (1H,d,J=12 Hz), 4.59 (1H,d,J=12 Hz), 5.45 (1H,s), 6.9–7.4 (9H,m), 7.48 (1H,d, J=1 Hz), 7.67 (1H,d,J=1 Hz)

MASS: 432 (M+H)$^+$

(13) 1-[(2S,3R)-2-(benzyloxy)-5-(2-phenethyloxyphenyl)-3-pentyl]imidazole-4-carboxamide was prepared from the compound obtained in Preparation 1 and the compound obtained in Preparation 11(8).

NMR (CDCl$_3$, δ): 0.99 (3H,d,J=6 Hz), 1.9–2.6 (4H,m), 3.06 (2H,t,J=7 Hz), 3.5–3.6 (1H,m), 3.8–4.6 (5H,m), 5.34 (1H,s), 6.7–7.0 (3H,m), 7.1–7.4 (13H,m), 7.62 (1H,d,J=1 Hz)

MASS: 484 (M+H)$^+$

(14) 1-[(2S,3R)-2-(benzyloxy)-5-(2,3-dimethylphenyl)-3-pentyl]-imidazole-4-carboxamide was prepared from the compound obtained in Preparation 1 and the compound obtained in Preparation 11(9).

NMR(CDCl$_3$, δ): 1.06 (3H,d,J=6 Hz), 2.0–2.6 (4H,m), 2.09 (3H,s), 2.26 (3H,s), 3.6–3.7 (1H,m), 3.9–4.0 (1H,m), 4.38 (1H,d,J=12 Hz), 4.58 (1H,d,J=12 Hz), 5.39 (1H,s), 6.7–7.4 (9H,m), 7.46 (1H,d,J=1 Hz), 7.67 (1H,d,J=1 Hz)

MASS: 392 (M+H)$^+$

(15) 1-{(2S,3R)-2-(benzyloxy)-5-[2-(trifluoromethyl)phenyl]-3-pentyl}imidazole-4-carboxamide was prepared from the compound obtained in Preparation 1 and the compound obtained in Preparation 28(1).

NMR (CDCl$_3$, δ): 1.09 (3H,d,J=6 Hz), 2.0–2.8 (4H,m), 3.6–3.8 (1H,m), 3.9–4.1 (1H,m), 4.39 (1H,d,J=12 Hz), 4.59 (1H,d,J=12 Hz), 5.40 (1H,s), 6.9–7.7 (12H,m)

MASS: 432 (M+H)$^+$

(16) 1-{(2S,3R)-2-(benzyloxy)-5-[2,3-(methylenedioxy)phenyl]-3-pentyl}imidazole-4-carboxamide was prepared from the compound obtained in Preparation 1 and the compound obtained in Preparation 11(10).

NMR (CDCl$_3$, δ): 1.06 (3H, d, J=6 Hz), 2.0–2.6 (4H, m), 3.6–4.0 (2H, m), 4.38 (1H, d, J=12 Hz), 4.58 (1H, d, J=12 Hz), 5.38 (1H, s), 5.90 (2H, s) , 6.4–6.8 (3H, m) , 6.96 (1H, s) , 7.2–7.4 (5H, m), 7.43 (1H, d, J=1 Hz) , 7.65 (1H, d, J=1 Hz)

MS: 408 (M+H)$^+$

(17) 1-[(2S,3R)-2-(tert-butyldimethylsilyloxy)-5-(2-benzyloxy-phenyl)-3-pentyl]imidazole-4-carboxamide was prepared from the compound obtained in Preparation 1 and the compound obtained in Preparation 28(3).

NMR (CDCl$_3$, δ): –0.07 (3H, s), –0.02 (3H, s), 0.84 (9H, s), 0.93 (3H, d, J=6 Hz), 1.8–2.8 (4H, m), 3.7–3.9 (2H, m), 5.07 (2H, s), 5.35 (1H, s), 6.8–7.4 (11H, m), 7.61 (1H, s)

MS: 494 (M+H)$^+$

(18) 1-[(2S,3R)-2-(benzyloxy)-5-(2-naphthyl)-3-pentyl]imidazole-4-carboxamide was prepared from the compound obtained in Preparation 1 and the compound obtained in Preparation 28(4).

IR (neat): 1662 cm$^{-1}$

NMR (CDCl$_3$, δ): 1.06 (3H, d, J=6 Hz), 2.1–2.9 (4H, m), 3.6–3.8 (1H, m), 3.8–4.1 (1H, m), 4.37 (1H, d, J=12 Hz), 4.57 (1H, d, J=12 Hz), 5.45 (1H, s), 7.0 (1H, s), 7.2–7.8 (14H, m)

MS: 414 (M+H)$^+$

(19) 1-[(2S,3R)-2-(benzyloxy)-6-(1-naphthyl)-3-hexyl]imidazole-4-carboxamide was prepared from the compound obtained in Preparation 1 and the compound obtained in Preparation 28(5).

IR (neat): 1658 cm$^{-1}$

NMR (CDCl$_3$, δ): 1.04 (3H, d, J=6 Hz), 1.5–2.3 (4H, m), 2.9–3.2 (2H, m), 3.5–3.7 (1H, m), 3.8–4.1 (1H, m), 4.37 (1H, d, J=12 Hz), 4.57 (1H, d, J=12 Hz), 5.51 (1H, s), 6.97 (1H, s) 7.1–8.0 (14H, m)

MS: 428 (M+H)$^+$

(20) Methyl 1-[(2S,3R)-2-benzyloxy-5-(1-naphthyl)-3-pentyl]-imidazole-4-carboxylate was prepared from (2S, 3S)-2-benzyloxy-5-(1-naphthyl)pentan-3-ol (obtained in Preparation 26) and methyl imidazole-4-carboxylate.

IR (neat): 2945, 1726, 1672 cm$^{-1}$

NMR (CDCl$_3$, d): 1.06 (3H, d, J=6.2 Hz), 2.15–2.60 (2H, m), 2.75–3.10 (2H, m), 3.65 (1H, m), 3.91 (3H, s), 3.96 (1H, m), 4.33 (1H, d, J=11.5 Hz), 4.55 (1H, d, J=11.5 Hz), 7.10–7.90 (14H, m)

MASS (APCI, m/z): 429 (M+H)$^+$

[α]$_D^{27}$+13.7° (c 0.65, EtOH)

EXAMPLE 4

Twenty percent palladium hydroxide on carbon (30 mg) was added to a stirred solution of 1-[(2S)-2-benzyloxy-5- phenyl-3-pentyl]imidazole-4-carboxamide (obtained in Example 3(1))(107 mg) in cyclohexene (5 ml) and ethanol (12.5 ml). The resulting mixture was stirred at reflux temperature for 12 hours. After cooling to room temperature, the mixture was filtered through Celite, and the insoluble material on the filter was washed with ethanol. The filtrate and washing were combined and then concentrated in vacuo. The resulting residue was purified by silica gel (3 g) chromatography eluted with chloroform/methanol (50:1) to give 1-[(2S)-2-hydroxy-5-phenyl-3-pentyl]imidazole-4-carboxamide (69.1 mg).

IR (KBr): 3338, 2969, 1658 cm$^{-1}$

NMR (DMSO-d$_6$, $\delta$): 0.84–0.93 (3H, m), 2.00–2.50 (4H, m), 3.70–4.00 (2H, m), 4.95–5.10 (1H, m), 6.95–7.40 (7H, m), 7.66 (1H, d, J=2.2 Hz), 7.72 (1H, d, J=4.1 Hz)

MASS: 274 (M+H)$^+$

EXAMPLE 5

The following compounds were obtained according to a similar manner to that of Example 4.

(1) 1-[(2S)-2-hydroxy-6-phenyl-3-hexyl]imidazole-4-carboxamide was prepared from the compound obtained in Example 3(2).

IR (KBr): 3700–2800, 1660, 1594 cm$^{-1}$

NMR (DMSO-d$_6$, $\delta$): 0.80–1.00 (3H, m), 1.15–1.55 (2H, m), 1.60–2.05 (2H, m), 2.40–2.70 (2H, m), 3.70–4.10 (2H, m), 4.95–5.10 (1H, m), 6.90–7.35 (7H, m), 7.60–7.75 (2H, m)

MASS: 288 (M+H)$^+$ (2) (2S)-2-hydroxy-5-(1-naphthyl)-3-pentylimidazole-4-carboxamide was prepared from the compound obtained in Example 3(3).

mp: 95–98° C.

IR (KBr): 3336, 1658, 1594 cm$^{-1}$

NMR (DMSO-d$_6$, $\delta$): 0.80–1.00 (3H, m), 2.05–2.45 (2H, m), 2.60–3.15 (2H, m), 3.70–4.20 (2H, m), 5.05–5.15 (1H, m), 7.07 (1H, brs), 7.20–7.60 (5H, m), 7.70–8.00 (5H, m)

MASS: 324 (M+H)$^+$

EXAMPLE 6

Triethylamine (1.06 g) was added dropwise to a stirred mixture of (R)-1-(tert-butyldimethylsilyl-oxy)-4-phenylbutan-2-ol (obtained in Preparation 14) (2.10 g) and methanesulfonyl chloride (1.20 g) in dichloromethane (20 ml) at ice-bath temperature. After 1 hour, the reaction mixture was partitioned between dichloromethane and water. The organic layer was washed with brine and dried over MgSO$_4$, and concentrated in vacuo to give the methanesulfonate (2.74 g) as an oil. This material was used for the next reaction without further purification.

NaH (60% in mineral oil, 299 mg) was added to a solution of methyl 4-imidazolecarboxylate (942 mg) in DMF (20 ml) at room temperature. The reaction mixture was stirred for 30 minutes. The methanesulfonate prepared above was added and the resulting mixture was stirred for 37 hours at 70° C.

The reaction mixture was cooled to 10° C. in an ice bath, and the insoluble material was filtered and washed thoroughly with dichloromethane. The filtrate and the washing were combined and then washed with brine. The organic layer was dried over sodium sulfate and concentrated in vacuo. The residue was purified by silica gel (50 g) column chromatography eluting with toluene/ethyl acetate (20:1) to give methyl (S)-1-[1-(tert-butyldimethylsilyloxy)-4-phenyl-2-butyl]imidazole-4-carboxylate (1.52 g).

IR (neat): 2950, 2933, 2857, 1725, 1675, 1189, 1122 cm$^{-1}$

NMR (CDCl$_3$, $\delta$): –0.06 (3H, s), –0.05 (3H, s), 0.84 (9H, s), 2.10–2.25 (2H, m), 2.35–2.75 (2H, m), 3.70–3.80 (2H, m), 3.91 (3H, s), 4.00 (1H, m), 7.05–7.38 (5H, m), 7.51 (1H, s), 7.69 (1H, s)

MASS: 3S9 (M+H)$^+$

EXAMPLE 7

A solution of 28% NaOMe in methanol (772 mg) was added to an ice cooled solution of aminoguanidine hydrochloride (332 mg) in methanol (5 ml). After 10 minutes, methyl (S)-1-[1-(tert-butyldimethylsilyloxy)-4-phenyl-2-butyl]-imidazole-4-carboxylate (obtained in Example 6) (389 mg) in methanol (2 ml) was added to the mixture and the resulting mixture was stirred at reflux for 22 hours. After cooling, the insoluble material was removed and then the filtrate was evaporated. The residue was diluted with water and the solution was acidified to pH 4 with 6N HClaq. The resulting mixture was washed with CHCl$_3$. The aqueous layer was purified by HP-20 (50 cc) column chromatography eluting with water/2-propanol (9:1) and lyophilized to give (S)-2-[4-(5-amino-1,2,4-triazol-3-yl)-1-imidazolyl]-4-phenylbutan-1-ol (107 mg).

mp: 80° C. (decompose)

IR (KBr): 3700–2700, 1641, 1602, 1238, 1058 cm$^{-1}$

NMR (DMSO-d$_6$, $\delta$): 1.95–2.60 (4H, m), 3.64 (2H, brs), 4.10 (1H, m), 5.02 (1H, brs), 5.40 (2H, br), 7.10–7.35 (6H, m), 7.55 (1H, s), 7.70 (1H, s)

MASS: 299 (M+H)$^+$

EXAMPLE 8

A solution of 28% NaOMe in methanol (583 mg) was added to an ice cooled solution of guanidine hydrochloride (307 mg) in DMF (5 ml). After 10 minutes, methyl (S)-1-[1-(tert-butyl-dimethylsilyloxy)-4-phenyl-2-butyl]imidazole-4-carboxylate (obtained in Example 6) (250 mg) in DMF (2 ml) was added to the mixture and the resulting mixture was stirred at 100° C. for 5 hours. After cooling, the reaction mixture was poured into water (30 ml) and the solution was washed with ethyl acetate. The aqueous layer was purified by HP-20 (40 cc) column chromatography eluting with water/2-propanol (9:1) and lyophilized to give (S)-1-[1-hydroxy-4-phenyl-2-butyl]imidazole-4-carbonylguanidine (55.4 mg)

mp: 111–113° C.

IR (KBr): 3700–2700, 1639, 1592, 1517, 1405 cm$^{-1}$

NMR (DMSO-d$_6$, $\delta$) 1.90–2.60 (4H, m), 3.62 (2H, d, J=5.0), 4.07 (1H, m), 5.02 (1H, brs), 7.00–8.00 (11H, m)

MASS: 302 (M+H)$^+$

EXAMPLE 9

To an ice cooled solution of 1-[1-(tert-butyldimethylsilyloxy)-4-(4-methylphenyl)-2-butyl]imidazole-4-carboxamide (obtained in Example 3(4))(194 mg, 0.50 mmol) in THF (5 ml) was added dropwise 1.0 M Bu$_4$NF in THF (1.0 ml). After the addition was completed, the reaction mixture was stirred at ice-bath temperature for 1 h. 25% AcONH$_4$ (4 ml) was added, and the resulting mixture was stirred for several minutes and then extracted with chloroform. The organic layer was washed with brine, dried (sodium sulfate) and concentrated in vacuo. The residue was purified by silica gel (5 g) column chromatography eluting with chloroform/methanol (20:1) to give 1-[1-hydroxy-4-(4-methylphenyl)-2-butyl]imidazole-4-carboxamide (44.9 mg, 32.9%) as a white solid.

mp: 138–141° C.

IR (KBr): 3320, 3193, 2852, 1693, 1668, 1606 cm$^{-1}$

NMR (DMSO-d$_6$, δ): 1.90–2.15 (2H, m), 2.20–2.50 (5H, m), 3.61 (2H, t, J=5.4 Hz), 4.08 (1H, m), 5.00 (1H, t, J=5.3 Hz), 6.90–7.15 (5H, m), 7.27 (1H, br s), 7.69 (1H, s), 7.74 (1H, s)

MASS: 274 (M+H)$^+$

EXAMPLE 10

The following compound was prepared by a similar procedure to that of Example 9.

(1) 1-{1-Hydroxy-4-[3-(ethoxycarbonyl)phenyl]-2-butyl}-imidazole-4-carboxamide was prepared from the compound obtained in Example 3(5).

mp: 92–95° C.

IR (KBr): 3322, 3193, 2954, 1720, 1662, 1604, 1278 cm$^{-1}$

NMR (DMSO-d$_6$, δ): 1.32 (3H, t, J=7.1 Hz), 2.00–2.20 (2H, m), 2.35–2.55 (2H, m), 3.64 (2H, br), 4.31 (2H, q, J=7.1 Hz), 5.03 (1H, br s), 7.03 (1H, br s), 7.26 (1H, br s), 7.40–7.50 (2H, m), 7.65–7.85 (4H, m)

MASS: 332 (M+H)$^+$ (2) 1-{1-Hydroxy-4-[3-(methoxycarbonylmethyl)phenyl]-2-butyl}imidazole-4-carboxamide was prepared from the compound obtained in Example 3(6).

mp: 138.5–141.0° C.

IR (KBr): 3600–3000, 2951, 1738, 1651, 1583, 1267 cm$^{-1}$

NMR (DMSO-d$_6$, δ): 1.90–2.20 (2H, m), 2.20–2.50 (2H, m), 3.50–3.75 (7H, m), 4.10 (1H, m), 5.01 (1H, t, J=5.3 Hz), 6.90–7.35 (6H, m), 7.70 (1H, s), 7.75 (1H, s)

MASS: 332 (M+H)$^+$ (3) 1-[(2S,3R)-2-hydroxy-5-(2-benzyloxyphenyl)-3-pentyl]-imidazole-4-carboxamide was prepared from the compound obtained in Example 3 (17).

NMR (CDCl$_3$, δ): 1.02 (3H, d, J=6 Hz), 1.9–2.8 (5H, m), 3.8–4.0 (2H, m), 5.07 (2H, s), 5.38 (1H, s), 6.8–7.4 (11H, m), 7.66 (1H, d, J=1 Hz)

MS: 380 (M+H)$^+$

[α]$_D^{27}$=+16.2° (c 1.0, EtOH)

EXAMPLE 11

Sodium methoxide (39 mg, 0.72 mmol) was added to a stirred solution of 1-{1-hydroxy-4-[3-(ethoxycarbonyl)phenyl]-2-butyl}-imidazole-4-carboxamide (obtained in Example 10(1))(60 mg, 0.18 mmol) in formamide (1.5 ml), and the reaction mixture was stirred at 110° C. for 3 h. After cooling, the reaction mixture was poured into water (5 ml). The residue was purified by HP-20 (16 cc) column chromatography eluting with water/2-propanol (9:1) and lyophilized to give 1[4-(3-carbamoylphenyl)-1-hydroxy-2-butyl]imidazole-4-carboxamide (39.2 mg, 71.6%) as an amorphous solid.

IR (KBr): 3700–2800, 1660, 1592, 1402 cm$^{-1}$

NMR (DMSO-d$_6$, δ): 2.09 (2H, m), 2.30–2.65 (2H, m), 3.64 (2H, t, J=5.4 Hz), 4.14 (1H, m), 5.04 (1H, t, J=5.3 Hz), 7.05 (1H, br s), 7.20–7.50 (4H, m), 7.65–7.85 (4H, m), 7.93 (1H, br s)

MASS: 332 (M+H)$^+$

EXAMPLE 12

The following compound was prepared by a similar procedure to that of Example 1.

(1) 1-{1-hydroxy-4-[3-(2-hydroxyethyl)phenyl]-2-butyl}-imidazole-4-carboxamide was prepared from the compound obtained in Example 10(2).

IR (KBr): 3700–3000, 2927, 2861, 1658, 1595, 1414, 1055 cm$^{-1}$

NMR (DMSO-d$_6$, δ): 1.90–2.20 (2H, m), 2.20–2.50 (2H, m), 2.68 (2H, t, J=7.1 Hz), 3.50–3.70 (4H, m), 4.10 (1H, m), 4.61 (1H, t, J=5.2 Hz), 5.01 (1H, t, J=5.4 Hz), 6.90–7.35 (6H, m), 7.70 (1H, s), 7.74 (1H, s)

MASS: 304 (M+H)$^+$ (2) 1-[1-Hydroxy-4-phenyl-2-butyl]imidazole-4-carbonitrile was prepared from the compound obtained in Preparation 23.

mp: 111–115° C.

IR (KBr): 3500–3000, 2943, 2867, 2237, 1078 cm$^{-1}$

NMR (DMSO-d$_6$, δ): 1.95–2.60 (4H, m), 3.55–3.70 (2H, m), 4.18 (1H, m), 5.06 (1H, t, J=5.4 Hz), 7.05–7.35 (5H, m), 7.93 (1H, s), 8.25 (1H, s)

MASS: 242 (M+H)$^+$

EXAMPLE 13

A mixture of methyl (S)-1-[1-(tert-butyldimethylsilyloxy)-4-phenyl-2-butyl]imidazole-4-carboxylate (obtained in Example 6) (300 mg, 0.77 mmol) and hydrazine monohydrate (5 ml) in DMF (3 ml) was stirred at 100° C. for 2 h.

After cooling, the reaction mixture was poured into water (10 ml) and extracted with ethyl acetate. The organic layer was washed with brine, dried over sodium sulfate and evaporated in vacuo. The residue was purified by silica gel (10 g) column chromatography eluting with chloroform/methanol (100:1) to give (S)-1-[1-(tert-butyldimethylsilyloxy)-4-phenyl-2-butyl]imidazole-4-carbohydrazide (274 mg, 91.5%).

IR (neat): 3700–3000, 2933, 2858, 1646, 1568, 1466, 1252, 1120 cm$^{-1}$

NMR (CDCl$_3$, δ): −0.07 (3H, s), −0.05 (3H, s), 0.83 (9H, s), 2.05–2.75 (4H, m), 3.65–4.10 (5H, m), 7.00–7.40 (5H, m), 7.43 (1H, s), 7.63 (1H, s)

MASS: 389 (M+H)$^+$

EXAMPLE 14

A powder of NaOMe (417 mg, 7.72 mmol) was added to an ice cooled solution of hydroxylamine hydrochloride (536 mg, 7.72 mmol) in methanol (5 ml). After 30 minutes, methyl (S)-1-[1-(tert-butyldimethylsilyloxy)-4-phenyl-2-butyl]imidazole-4-carboxylate (obtained in Example 6)(389 mg, 1.0 mmol) in methanol (2 ml) was added to the mixture and the resulting mixture was stirred at reflux for 3 day. After cooling, the insoluble material was removed and then the filtrate was evaporated. The residue was diluted with water and the solution was acidified to pH 4 with 1N HClaq. The resulting mixture was washed with CHCl$_3$. The aqueous layer was purified by HP-20 (40 cc) column chromatography eluting with water/2-propanol (9:1) and lyophilized to give (S)-1-[1-hydroxy-4-phenyl-2-butyl]-imidazole-4-carbohydroxamic acid (92.5 mg, 43.5%) as an amorphous solid.

IR (neat): 3700–2700, 1645, 1566, 1238, 1141 cm$^{-1}$

NMR (DMSO-d$_6$, δ): 1.90–2.60 (4H, m), 3.63 (2H, m), 4.10 (1H, m), 5.01 (1H, br), 7.05–7.40 (5H, m), 7.70 (1H, s), 7.76 (1H, s), 8.72 (1H, br), 10.62 (1H, br s)

MASS: 276 (M+H)$^+$

EXAMPLE 15

A powder of NaOMe (67.2 mg, 1.24 mmol) was added to a solution of hydroxylamine hydrochloride (86.4 mg, 1.24 mmol) in methanol (2 ml) at room temperature. After 30 minutes, 1-(1-hydroxy-4-phenyl-2-butyl)imidazole-4-carbonitrile (obtained in Example 12(2))(100 mg, 0.41 mmol) was added to the mixture and the resulting mixture was stirred at reflux for 2 h. After cooling, the insoluble material was removed and then the filtrate was evaporated. The residue was purified by silica gel (5 g) column chromatography eluting with chloroform/methanol (20:1) and concentrated in vacuo. The residue was triturated with isopropyl ether to give N-hydroxy-1-[1-hydroxy-4-phenyl-2-butyl]imidazole-4-carboximidamide (86.3 mg, 76.0%) as an amorphous solid.

IR (KBr): 3700–2800, 1649, 1604, 1496 cm$^{-1}$

NMR (DMSO-d$_6$, δ): 1.90–2.60 (4H, m), 3.62 (2H, t, J=4.9 Hz), 4.09 (1H, m), 5.04 (1H, t, J=5.2 Hz), 6.06 (2H, br s), 7.10–7.40 (5H, m), 7.58 (1H, s), 7.75 (1H, s), 9.41 (1H, br s)

MASS: 275 (M+H)$^+$

EXAMPLE 16

A mixture of 1-(1-hydroxy-4-phenyl-2-butyl)imidazole-4-carbonitrile (obtained in Example 12(2))(100 mg, 0.41 mmol), ammonium chloride (111 mg, 2.07 mmol) and sodium azide (135 mg, 2.07 mmol) in DMF (4 ml) was stirred at 100° C. for 8 h.

After cooling, the reaction mixture was poured into water (30 ml) and the solution was washed with CHCl$_3$. The aqueous layer was purified by HP-20 (16 cc) column chromatography eluting with water/2-propanol (9:1) and lyophilized to give 1-(1-hydroxy-4-phenyl-2-butyl)-4-(5-tetrazolyl)imidazole (63.3 mg, 53.8%) as an amorphous solid.

IR (KBr): 3700–2700, 1651, 1612, 1496, 1458, 1250 cm$^{-1}$

NMR (DMSO-d$_6$, δ): 1.95–2.60 (4H, m), 3.66 (2H, m), 4.09 (1H, m), 5.03 (1H, br), 7.05–7.35 (5H, m), 7.55 (1H, s), 7.68 (1H, s), 9.41 (1H, br s)

MASS: 285 (M+H)$^+$

EXAMPLE 17

A suspension of imidazole-4-carboxamide (obtained in Preparation 1)(207 mg) in DMF (3 ml) was treated with sodium hydride (60% in mineral oil, 87 mg) at ice-bath temperature and the mixture was stirred at room temperature for 20 min. A solution of (2S,3S)-2-benzyloxy-5-(1-nephthyl)-3-pentyl methanesulfonate (obtained in Preparation 27)(0.62 mg) in DMF (5 ml) was added and the mixture was stirred at 80° C. for 48 h. After cooling, the mixture was filtered to remove the insoluble material. The filtrate was poured into water and extracted with ethyl acetate. The extract was washed with water and brine, dried and concentrated in vacuo. Flash chromatography (dichloromethane:methanol=50:1) gave 1-[(2S,3R)-2-benzyloxy-5-(1-naphthyl)-3-pentyl]imidazole-4-carboxamide (221 mg, 34.4%) as an oil.

IR (neat): 3458, 3332, 3184, 1666, 1593 cm$^{-1}$

NMR (CDCl$_3$, d): 1.04 (3H, d, J=6.3 Hz), 2.15–2.60 (2H, m), 2.80–3.10 (2H, m), 3.64 (1H, m), 3.98 (1H, m), 4.53 (1H, d, J=11.6 Hz), 4.55 (1H, d, J=11.6 Hz), 5.49 (1H, bs), 7.00 (1H, bs), 7.15–7.90 (14H, m)

MASS (APCI, m/z): 414 (M+H)$^+$ $[α]_D^{27}$+23.7° (c 0.5, EtOH)

EXAMPLE 18

The following compounds were obtained according to the procedure of Example 17.
(1) 1-[(2S,3S)-2-benzyloxy-5-(1-naphthyl)-3-pentyl] imidazole-4-carboxamide was prepared from (2S,3R)-2-benzyloxy-5-(1-naphthyl)-3-pentyl) methanesulfonate (obtained in Preparation 29(1))(1.99 g) and imidazole-4-carboxamide (0.67 g).

IR (neat): 3460, 3330, 3182, 1668, 1593 cm$^{-1}$

NMR (CDCl$_3$, d): 1.03 (3H, d, J=6.2 Hz), 2.15–2.55 (2H, m), 2.74–3.03 (2H, m), 3.66 (1H, m), 3.86 (1H, m), 4.26 (1H, d, J=11.6 Hz), 4.56 (1H, d, J=11.6 Hz), 5.52 (1H, bs), 7.02 (1H, bs), 7.12–7.50 (10H, m), 7.71–7.88 (4H, m)

MASS (APCI, m/z): 414 (M+H)$^+$ $[α]_D^{26}$−21.1° (c 0.5, EtOH)

(2) 1-[(2S,3R)-2-(tert-butyldimethylsilyloxy)-5-phenyl-3-pentyl]imidazole-4-carboxamide was prepared from (2S, 3S)-4-(tert-butyldimethylsilyloxy)-5-phenyl-3-pentyl methanesulfonate (obtained in Preparation 29(2)) and imidazole-4-carboxamide (obtained in Preparation 1) according to the procedure of Example 17.

IR (neat): 3465, 3332, 3188, 2935, 1672, 1599 cm$^{-1}$

NMR (CDCl$_3$, d): −0.24 (3H, s), 0.10 (3H, s), 0.88 (9H, s), 0.98 (3H, d, J=6.1 Hz), 2.09 (1H, m), 2.20–2.45 (2H, m), 2.62 (1H, m), 3.77 (1H, m), 3.88 (1H, m), 5.47 (1H, bs), 6.98 (1H, bs), 7.06 (2H, d, J=6.4 Hz), 7.20–7.33 (3H, m), 7.38 (1H, d, J=1.1 Hz), 7.62 (1H, d, J=1.1 Hz)

MS (APCI, m/z): 388 (M+H)$^+$ $[α]_D^{27}$+29.3° (c 0.5, EtOH)

EXAMPLE 19

The following compound was prepared by a similar procedure to that of Example 9.
(1) (S)-1-[1-hydroxy-4-phenyl-2-butyl]imidazole-4-carbohydrazide was prepared as an amorphous solid from the compound obtained in Example 13.

NMR (DMSO-d$_6$, δ): 2.00–2.55 (4H, m), 3.63 (2H, t, J=5.2 Hz), 4.10 (1H, m), 4.33 (2H, br), 5.01 (1H, t, J=5.3 Hz), 7.10–7.35 (5H, m), 7.70 (1H, s), 7.77 (1H, s), 8.97 (1H, br s)

MASS: 275 (M+H)$^+$ (2) 1-[(2S,3R)-2-hydroxy-5-phenyl-3-pentyl]imidazole-4-carboxamide was prepared from the compound obtained in Example 18(2).

IR (KBr): 3336, 1658, 1593 cm$^{-1}$

NMR (DMSO-d$_6$, d): 0.87 (3H, d, J=6.0 Hz), 2.00–2.40 (4H, m), 3.75–3.95 (2H, m), 5.08 (1H, d, J=4.8 Hz), 7.07 (1, bs), 7.10–7.30 (6H, m), 7.72 (1H, s), 7.74 (1H, s)

MS (APCI, m/z): 274(M+H)$^+$ $[α]_D^{26}$+43.5° (c 0.4, EtOH)

EXAMPLE 20

A mixture of methyl 1-[(2S,3R)-2-benzyloxy-5-(1-naphthyl)-3-pentyl]imidazole-4-carboxylate (obtained in Example 3(20)) (160 mg) in ammonium hydroxide (10 ml) and DMF (5 ml) was heated at 100° C. for 8 h in a sealed tube and then concentrated in vacuo. Flash chromatography (dichloromethane:methanol=20:1) gave 1-[(2S,3R)-2-benzyloxy-5-(1-naphthyl)-3-pentyl]imidazole-4-carboxamide (144 mg, 93.3%) as an oil.

EXAMPLE 21

1-[(2S,3R)-2-benzyloxy-5-(1-naphthyl)-3-pentyl] imidazole-4-carboxamide (obtained in Example 17 or 20) (5.07 g) was dissolved in a mixture of ethanol (300 ml) and cyclohexene (150 ml) and then palladium hydroxide (20% on carbon, 5.0 g) was added. The mixture was heated under reflux for 3 days. After cooling, the catalyst was filtered and washed with ethanol. The combined filtrate and washings were concentrated in vacuo. Flash chromatography (dichloromethane:methanol=10:1) gave 1-[(2S,3R)-2-hydroxy-5-(1-naphthyl)-3-pentyl]imidazole-4-carboxamide (2.71 g, 68.4%) as a foam.

IR (KBr): 3334, 1666, 1593 cm$^{-1}$

NMR (DMSO-d$_6$, d): 0.88 (3H, d, J=6.2 Hz), 2.10–2.40 (2H, m), 2.60–2.95 (2H, m), 3.83 (1H, m), 4.05 (1H, m), 5.09 (1H, d, J=4.9 Hz), 7.10 (1H, bs), 7.25 (1H, d, J=6.3 Hz), 7.34 (1H, bs), 7.42 (1H, t, J=7.6 Hz), 7.49–7.54 (2H, m), 7.76–7.94 (5H, m)

MASS (APCI, m/z): 324 (M+H)$^+$ $[\alpha]_D^{27}$+29.2° (c 0.5, EtOH)

EXAMPLE 22

1-[(2S,3S)-2-hydroxy-5-(1-naphthyl)-3-pentyl]-imidazole-4-carboxamide was prepared from the compound obtained in Example 18(1) according to a similar procedure to Example 21.

IR (KBr): 3334, 1658, 1593 cm$^{-1}$

NMR (DMSO-d$_6$, d): 0.91 (3H, d, J=6.3 Hz), 2.10–2.30 (2H, m), 2.60–3.05 (2H, m), 3.95 (1H, m), 4.13 (1H, m), 5.05 (1H, d, J=4.1 Hz), 7.06 (1H, bs), 7.25–7.55 (5H, m), 7.75–7.95 (5H, m)

MASS (APCI, m/z): 324 (M+H)$^+$ $[\alpha]_D^{27}$-22.4° (c 0.25, EtOH)

EXAMPLE 23

The following compound was prepared by a similar procedure to that of Example 4.

(1) 1-[(2S,3R)-2-hydroxy-5-(2-methylphenyl)-3-pentyl]imidazole-4-carboxamide was prepared from the compound obtained in Example 3(8).

mp: 60–62° C.

NMR (CDCl$_3$, δ): 1.11 (3H,d,J=6 Hz), 2.0–2.6 (5H,m), 2.20 (3H,s), 3.8–4.1 (2H,m), 5.47 (1H,s), 6.9–7.2 (5H,m), 7.46 (1H,d,J=1 Hz), 7.73 (1H,d,J=1 Hz)

MASS: 288 (M+H)$^+$ $[\alpha]_D^{25}$=+110.5° (c 0.50, EtOH)

(2) 1-[(2S,3R)-2-hydroxy-5-(2-methoxyphenyl)-3-pentyl]-imidazole-4-carboxamide was prepared from the compound obtained in Example 3(10).

NMR(CDCl$_3$, δ): 1.09 (3H,d,J=6 Hz), 2.0–2.7 (5H,m), 3.81 (3H,s), 3.9–4.0 (2H,m), 5.40 (1H,s), 6.8–7.3 (5H,m), 7.46 (1H,d,J=1 Hz), 7.72 (1H,d,J=1 Hz)

MASS: 304 (M+H)$^+$ $[\alpha]_D^{25}$=+110.0° (c 0.50, EtOH)

(3) 1-[(2S,3R)-2-hydroxy-5-(2-hexyloxyphenyl)-3-pentyl]-imidazole-4-carboxamide was prepared from the compound obtained in Example 3(11).

NMR (CDCl$_3$, δ): 0.8–1.0 (3H,m), 1.09 (3H,d,J=6 Hz), 1.2–1.5 (6H,m), 1.7–1.9 (3H,m), 2.0–2.7 (4H,m), 3.8–4.0 (4H,m), 5.35 (1H,s), 6.8–7.3 (5H,m), 7.45 (1H,s), 7.69 (1H,s)

MASS: 374 (M+H)$^+$ $[\alpha]_D^{28}$=+22.9° (c 0.50, EtOH)

(4) 1-[(2S,3R)-2-hydroxy-5-(2-hydroxyphenyl)-3-pentyl]-imidazole-4-carboxamide was prepared from the compound obtained in Example 3(13).

NMR (DMSO-d$_6$, δ): 0.87 (3H,d,J=6 Hz), 1.9–2.4 (4H, m), 3.7–4.0 (2H,m), 5.05 (1H,d,J=5 Hz), 6.6–7.3 (6H,m), 7.71 (2H,s), 9.29 (1H,s)

MASS: 290 (M+H)$^+$ (5) 1-[(2S,3R)-2-hydroxy-5-(2,3-dimethylphenyl)-3-pentyl]-imidazole-4-carboxamide was prepared from the compound obtained in Example 3(14).

NMR(CDCl$_3$, δ) 1.10 (3H,d,J=6 Hz), 2.0–2.6 (5H,m), 2.11 (3H,s), 2.26 (3H,s), 3.9–4.0 (2H,m), 5.43 (1H,s), 6.8–7.1 (4H,m), 7.47 (1H,d,J=1 Hz), 7.72 (1H,d,J=1Hz)

MASS: 302 (M+H)$^+$ $[\alpha]_D^{26}$=+26.7° (c 0.50, EtOH)

(6) 1-[(2S,3R)-2-hydroxy-5-[2-(trifluoromethyl)phenyl]-3-pentyl]imidazole-4-carboxamide was prepared from the compound obtained in Example 3(15).

NMR (CDCl$_3$, δ): 1.13 (3H,d,J=6 Hz), 2.0–2.4 (3H,m), 2.5–2.8 (2H,m), 3.9–4.1 (2H,m), 5.42 (1H,s), 6.9–7.8 (7H, m)

MASS: 342 (M+H)$^+$ $[\alpha]_D^{25}$=-0.70° (c 0.50, EtOH)

(7) Methyl 1-[(2S,3R)-2-hydroxy-5-(1-naphthyl)-3-pentyl]-imidazole-4-carboxylate was prepared from the compound obtained in Example 3(20).

NMR (CDCl$_3$, δ): 1.09 (3H,d,J=6 Hz), 1.9–2.6 (3H,m), 2.8–3.2 (2H,m), 3.92 (3H,s), 3.9–4.1 (2H,m), 7.1–7.9 (9H, m)

MASS: 339 (M+H)$^+$ (8) 1-{(2S,3R)-2-hydroxy-5-[2,3-(methylenedioxy)phenyl]-3-pentyl}imidazole-4-carboxamide was prepared from the compound obtained in Example 3(16).

NMR (CDCl$_3$, δ): 1.11 (3H, d, J=6 Hz), 2.1–2.7 (5H, m), 3.8–4.1 (2H, m), 5.44 (1H, s), 5.92 (2H, s), 6.5–6.8 (3H, m), 6.99 (1H, s), 7.44 (1H, d, J=1 Hz), 7.70 (1H, d, J=1 Hz)

MS: 318 (M+H)$^+$ $[\alpha]_D^{27}$=+29.3° (c 0.50, EtOH)

(9) 1-[(2S,3R)-2-hydroxy-5-(2-naphthyl)-3-pentyl]imidazole-4-carboxamide was prepared from the compound obtained in Example 3(18).

IR (KBr): 3340, 1658 cm$^{-1}$

NMR (CDCl$_3$, δ): 1.10 (3H, d, J=6 Hz), 2.1–2.4 (3H, m), 2.4–2.7 (1H, m), 2.7–2.9 (1H, m), 3.8–4.1 (2H, m), 5.46 (1H, s), 7.00 (1H, s), 7.2–7.9 (9H, m)

MS: 324 (M+H)$^+$ $[\alpha]_D^{26}$=+55.4° (c 0.50, EtOH)

(10) 1-[(2S,3R)-2-hydroxy-6-(1-naphtyl)-3-hexyl]imidazole-4-carboxamide was prepared from the compound obtained in Example 3(19).

IR (KBr): 3340, 1658 cm$^{-1}$

NMR (CDCl$_3$, δ): 1.08 (31H, d, J=6 Hz), 1.5–2.2 (5H, m), 3.06 (2H, t, J=8 Hz), 3.8–4.0 (2H, m), 5.48 (1H, s), 6.98 (1H, s), 7.2–8.0 (9H, m)

MS: 338 (M+H)$^+$

EXAMPLE 24

A mixture of 1-[(2S,3R)-2-(benzyloxy)-5-(2-chlorophenyl)-3-pentyl]imidazole-4-carboxamide (obtained in Example 3(9))(40 mg) and iodotrimethylsilane (0.02 ml) in chloroform (1 ml) was stirred at room temperature for 2 hours. The mixture was poured into methanol and the whole was evaporated in vacuo. The residue was taken up in ethyl acetate, washed with water, aqueous sodium bisulfite and sodium bicarbonate, successively, and dried. The residue left after evaporation of solvent was purified by column chromatography on silica gel, eluting with a mixture of dichloromethane and methanol (20:1) to give a white powder of 1-[(2S,3R)-2-hydroxy-5-(2-chlorophenyl)-3-pentyl] imidazole-4-carboxamide (6.1 mg).

NMR (CDCl$_3$, δ): 1.12 (3H,d,J=6 Hz), 1.9–2.4 (3H,m), 2.5–2.7 (2H,m), 3.9–4.1 (2H,m), 5.40 (1H,s), 6.9–7.4 (5H, m), 7.49 (1H,d,J=1 Hz), 7.72 (1H,d,J=1 Hz)

MASS: 308 (M+H)$^+$ $[\alpha]_D^{28}$=+17.9° (c 0.50, EtOH)

EXAMPLE 25

1-[(2S,3R)-2-Hydroxy-5-(2,3-dichlorophenyl)-3-pentyl]-imidazole-4-carboxamide was prepared by a similar procedure to that of Example 24 from the compound obtained in Example 3(12).

mp: 70–75° C.

NMR (CDCl$_3$, δ): 1.13 (3H,d,J=6 Hz), 1.98 (1H,d,J=5 Hz), 2.1–2.4 (2H,m), 2.6–2.8 (2H,m), 3.9–4.1 (2H,m), 5.39 (1H,s), 6.9–7.4 (4H,m), 7.49 (1H,d,J=1 Hz), 7.72 (1H,d,J=1 Hz)

MASS: 342 (M+H)$^+$ $[\alpha]_D^{28}$=+9.30° (c 0.50, EtOH)

EXAMPLE 26

Methyl 1-[(2S,3R)-2-(benzyloxy)-5-(1-naphthyl)-3-pentyl]imidazole-4-carboxylate was prepared by a similar procedure to that of Example 6 from methyl 4-imidazolecarboxylate and the compound obtained in Preparation 27.

NMR (CDCl$_3$, δ): 1.06 (3H,d,J=6 Hz), 2.1–2.6 (2H,m), 2.7–3.1 (2H,m), 3.6–3.7 (1H,m), 3.97 (3H,s), 3.9–4.1 (1H, m), 4.33 (1H,d,J=11 Hz), 4.56 (1H,d,J=11 Hz), 7.1–7.9 (14H,m)

MASS: 429 (M+H)$^+$

EXAMPLE 27

1-[(2S,3R)-2-hydroxy-5-(1-naphthyl)-3-pentyl] imidazole-4 -carbonylguanidine acetic acid salt was prepared by a similar procedure to that of Example 8 from the compound obtained in Example 23(7).

NMR(DMSO-d$_6$ δ): 0.90 (3H,d,J=6 Hz), 1.88 (3H,s), 2.1–2.5 (2H,m), 2.6–3.0 (2H,m), 3.8–4.2 (2H,m), 5.15 (1H, br s), 7.2–8.0 (9H,m)

MASS: 366 (M+H)$^+$ $[\alpha]_D^{26}$=+17.5° (c 0.50, EtOH)

EXAMPLE 28

A mixture of 1-[(2S,3R)-2-hydroxy-5-(2-hydroxyphenyl)-3-pentyl]imidazole-4-carboxamide (obtained in Example 23(4)) (4.1 mg), 1-bromo-3-phenylpropane (7 mg), and potassium carbonate (4 mg) in N,N-dimethylformamide (0.5 ml) was stirred overnight at room temperature. The mixture was taken up in ethyl acetate, washed twice with water, dried, and evaporated. The residue was purified by column chromatography on silica gel, eluting with a mixture of dichloromethane and methanol (20:1) to give a colorless gummy oil of 1-{(2S,3R)-2-hydroxy-5-[2-(3-phenylpropoxy)phenyl]-3-pentyl}imidazole-4-carboxamide (4.9 mg).

NMR (CDCl$_3$, δ): 1.08 (3H, d, J=6 Hz), 2.0–2.9 (9H, m), 3.9–4.0 (4H, m), 5.39 (1H, s), 6.7–7.4 (10H, m), 7.45 (1H, s), 7.71 (1H, s)

MS: 408 (M+H)$^+$

EXAMPLE 29

A mixture of methyl 1-[(2S,3R)-2-hydroxy-5-(1-naphthyl)-3-pentyl]imidazole-4-carboxylate (obtained in Example 23(7))(25 mg) and methylamine (40% in water; 1 ml) in tetrahydrofuran (3 ml) was heated in a steel sealed tube at 120° C. overnight. The mixture was taken up in dichloromethane, washed with water, dried, and evaporated. The residue was purified by column chromatography on silica gel, eluting with a mixture of dichloromethane and methanol (30:1) to give a white powder of N-methyl-1-[(2S, 3R)-2-hydroxy-5-(1-naphthyl)-3-pentyl]imidazole-4-carboxamide (18.6 mg).

NMR (CDCl$_3$, δ): 1.07 (3H, d, J=6 Hz), 2.1–2.5 (3H, m), 2.7–3.1 (2H, m), 3.01 (3H, d, J=7 Hz), 3.8–4.0 (2H, m), 7.0–7.9 (10H, m)

MS: 338 (M+H)$^+$ $[\alpha]_D^{27}$=+24.7° (c 0.50, EtOH)

EXAMPLE 30

A mixture of methyl 1-[(2S,3R)-2-benzyloxy-5-(1-naphthyl)- 3-pentyl]imidazole-4-carboxylate (obtained in Example 3(20))(97 mg) and sodium hydroxide (12 mg) in ethanol (2 ml) and water (0.2 ml) was stirred at room temperature overnight. The solvent was evaporated and the residue was taken up in a mixture of ethyl acetate and water. The aqueous layer was separated, acidified to pH 3 with hydrochloric acid, and extracted with ethyl acetate. The extract was dried and evaporated to give a pale brown powder of 1-[(2S,3R)-2-benzyloxy-5-(1-naphthyl)-3-pentyl]imidazole-4-carboxylic acid (84.5 mg).

NMR (CDCl$_3$, δ): 1.07 (3H, d, J=6 Hz), 2.2–2.6 (2H, m), 2.8–3.2 (2H, m), 3.5–3.7 (1H, m), 3.9–4.1 (1H, m), 4.34 (1H, d, J=12 Hz), 4.55 (1H, d, J=12 Hz), 7.1–7.9 (14H, m)

MS: 415 (M+H)$^+$

EXAMPLE 31

A mixture of 1-[(2S,3R)-2-benzyloxy-5-(1-naphthyl)-3-pentyl]imidazole-4-carboxylic acid (obtained in Example 30)(55 mg), methanesulfonamide (12.7 mg), 4-dimethylaminopyridine (24.3 mg), and 1-ethyl-3-(3'-dimethylaminopropyl)carbodiimide hydrochloride (51.2 mg) in N,N-dimethylformamide (2 ml) was stirred at room temperature for three days. Ethyl acetate and water were added, and the whole was acidified to pH 3 with hydrochloric acid. The organic layer was dried and evaporated. The residue was purified by column chromatography on silica gel, eluting with a mixture of dichloromethane and methanol (20:1) to give a pale yellow gummy oil of N-methylsulfonyl-1-[(2S,3R)-2-benzyloxy-5-(1-naphthyl)-3-pentyl] imidazole-4-carboxamide (18 mg).

NMR (CDCl$_3$, δ): 1.05 (3H, d, J=6 Hz), 2.2–2.5 (2H, m), 2.8–3.1 (2H, m), 3.40 (3H, s), 3.6–3.7 (1H, m), 3.9–4.1 (1H, m), 4.2–4.6 (2H, m), 7.0–7.9 (14H, m)

MS: 490 (M–H)$^-$

EXAMPLE 32

N-methylsulfonyl-1-[(2S,3R)-2-hydroxy-5-(1-naphthyl)-3-pentyl]imidazole-4-carboxamide was prepared from the compound obtained in Example 31 according to the procedure of Example 4.

NMR (CDCl$_3$+CD$_3$OD, δ): 0.97 (3H, d, J=6 Hz), 2.0–2.3 (2H, m), 2.7–3.1 (2H, m), 3.06 (3H, s), 3.8–4.1 (2H, m), 7.1–7.9 (9H, m)

MS: 402 (M+H)$^+$

INDUSTRIAL APPLICABILITY

The imidazole compounds of the present invention have ADA inhibitory activity and can thus elevate Ado concentration. Since Ado is effective for immunomodulation, especially immunosuppression, antiinflammation and treatment and prevention of various diseases, the imidazole compounds of the present invention are useful for treating or preventing diseases for which Ado is effective.

What is claimed is:

1. A compound of the formula

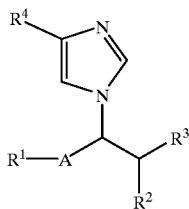

wherein
- $R^1$ is hydrogen, hydroxy, protected hydroxy, unsubstituted aryl or aryl substituted with at least one substituent selected from the group consisting of halo(lower)alkyl, halogen, hydroxy, protected carboxy, carbamoyl, lower alkylenedioxy, lower alkoxy optionally substituted with aryl, and lower alkyl optionally substituted with hydroxy or protected carboxy;
- $R^2$ is hydrogen or lower alkyl;
- $R^3$ is hydroxy or protected hydroxy;
- $R^4$ is cyano, (hydroxy)iminoamino(lower)alkyl, carboxy, protected carboxy, heterocyclic group optionally substituted with amino, unsubstituted carbamoyl or carbamoyl substituted with at least one substituent selected from the group consisting of amino, hydroxy, lower alkyl, lower alkylsulfonyl and aminoimino(lower)alkyl optionally substituted with hydroxy; and
- —A— is —Q— or —O—Q—, wherein Q is single bond or lower alkylene,
- provided that when $R^2$ is lower alkyl, then $R^1$ is hydroxy, protected hydroxy, or aryl optionally substituted with at least one substituent selected from the group consisting of halo(lower)alkyl, halogen, hydroxy, protected carboxy, carbamoyl, lower alkylenedioxy, lower alkoxy optionally substituted with aryl, and lower alkyl optionally substituted with hydroxy or protected carboxy;

its prodrug, or its salt.

2. The compound according to claim 1, wherein
- $R^1$ is aryl optionally substituted with at least one substituent selected from the group consisting of halo(lower)alkyl, halogen, hydroxy, protected carboxy, carbamoyl, lower alkylenedioxy, lower alkoxy optionally substituted with aryl, and lower alkyl optionally substituted with hydroxy or protected carboxy;
- $R^4$ is carbamoyl optionally substituted with at least one substituent selected from the group consisting of amino, hydroxy, lower alkyl, lower alkylsulfonyl and aminoimino(lower)alkyl optionally substituted with hydroxy; and
- —A— is lower alkylene.

3. The compound according to claim 2, wherein
- $R^1$ is phenyl or naphthyl, each of which are optionally substituted with at least one substituent selected from the group consisting of halo(lower)alkyl, halogen, hydroxy, protected carboxy, carbamoyl, lower alkylenedioxy, lower alkoxy optionally substituted with aryl, and lower alkyl optionally substituted with hydroxy or protected carboxy; and
- $R^4$ is carbamoyl.

4. The compound according to claim 1, which is a compound selected from the group consisting of:

(1) 1-(1-hydroxy-4-phenyl-2-butyl)imidazole-4-carboxamide;

(2) 1-[(2S)-2-hydroxy-5-phenyl-3-pentyl]imidazole-4-carboxamide;

(3) 1-[(2S,3R)-2-hydroxy-5-(2-benzyloxyphenyl)-3-pentyl]-imidazole-4-carboxamide;

(4) 1-[(2S,3R)-2-hydroxy-5-(1-naphthyl)-3-pentyl]imidazole-4-carboxamide;

(5) 1-[(2S,3R)-2-hydroxy-5-(2-hexyloxyphenyl)-3-pentyl]-imidazole4-carboxamide;

(6) 1-[(2S,3R)-2-hydroxy-5-(2-naphthyl)-3-pentyl]imidazole-4-carboxamide;

(7) 1-[(2S,3R)-2-hydroxy-5-(2-chlorophenyl)-3-pentyl]imidazole-4-carboxamide;

(8) 1-[(2S,3R)-2-hydroxy-5-(2,3-dichlorophenyl)-3-pentyl]-imidazole-4-carboxamide;

(9) 1-[(2S,3R)-2-hydroxy-5-(1-naphthyl)-3-pentyl]imidazole-4-carbonylguanidine; and

(10) 1-{(2S,3R)-2-hydroxy-5-[2-(3-phenylpropoxy)phenyl]-3-pentyl}imidazole-4-carboxamide.

5. A pharmaceutical composition comprising the compound of claim 1 as an active ingredient and a pharmaceutically acceptable, substantially non-toxic carrier or excipient.

6. A pharmaceutical composition having an adenosine deaminase inhibiting activity, which comprises the compound of claim 1 as an active ingredient and a pharmaceutically acceptable, substantially non-toxic carrier or excipient.

7. A method for inhibiting adenosine deaminase, which comprises administering the compound of claim 1 to a mammal in need of the compound.

8. A process for producing the compound of claim 1, comprising reacting a compound of formula (III)

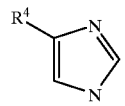

wherein $R^4$ is as defined above, with a compound of formula (IV)

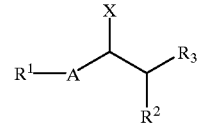

wherein $R^1$, $R^2$, $R^3$, and A are as defined above, and X is hydroxy or a leaving group, provided that $R^3$ is not hydroxy.

9. A process for producing the compound of claim 1, comprising reacting a compound of the formula (II)

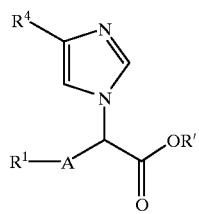

(II)

wherein $R^1$ and $R^4$ are as defined above and R' is a hydroxy protective group, with a reducing agent.

10. A method of using the compound of claim 1 for treating and/or preventing an autoimmune disease; an inflammatory condition; organ or tissue allo-or xeno-transplant rejection; leukemia; or a disease that arise from, or is aggravated by, insufficient blood flow through an organ or a portion thereof, comprising:

administering the compound of claim 1 to a subject in need thereof.

11. The process according to claim 9, wherein said reducing agent is sodium borohydride.

* * * * *

UNITED STATES PATENT AND TRADEMARK OFFICE
CERTIFICATE OF CORRECTION

| | | |
|---|---|---|
| PATENT NO. | : 6,359,145 B1 | Page 1 of 1 |
| DATED | : March 19, 2002 | |
| INVENTOR(S) | : Tadashi Terasaka et al. | |

It is certified that error appears in the above-identified patent and that said Letters Patent is hereby corrected as shown below:

<u>Title page,</u>
Item [75], Inventors:
"Tadashi Terasaka, Ikeda" should read -- Tadashi Terasaka, Osaka --;
"Katsuya Nakamura, Takatsuki" should read -- Katsuya Nakamura, Osaka --;
"Nobuo Seki, Takarazuka" should read -- Nobuo Seki, Hyogo --;
"Masako Kuno, Amagasaki" should read -- Masako Kuno, Hyogo --;
"Susumu Tsujimoto, Fujiidera" should read -- Susumu Tsujimoto, Osaka --;
"Akihiro Sato, Kobe" should read -- Akihiro Sato, Hyogo --;
"Isao Nakanishi, Tenri" should read -- Isao Nakanishi, Nara --;
"Takayoshi Kinoshita, Tsukuba" should read -- Takayoshi Kinoshita, Ibaraki --;
"Nobuya Nishio, Yawara-mura" should read -- Nobuya Nishio, Ibaraki --;
"Kiyoshi Tsuji, Kishiwada" should read -- Kiyoshi Tsuji, Osaka --.

Item [56], References Cited, "C. Vargeese, et al., Journal of Medicinal Chemistry, vol. 37, No. 22, pp. 384-3849," should read -- C. Vargeese, et al., Journal of Medicinal Chemistry, vol. 37, No. 22, pp. 3844-3849. --

<u>Column 4,</u>
Line 62, "group containing I to 4" should read -- group containing 1 to 4 --.

<u>Column 13,</u>
Line 35, "cm-1" should read -- $cm^{-1}$ --.

<u>Column 18,</u>
Line 11, "cm" should read -- $cm^{-1}$ --.

Signed and Sealed this

Third Day of December, 2002

JAMES E. ROGAN
*Director of the United States Patent and Trademark Office*